(12) United States Patent
Literati Nagy et al.

(10) Patent No.: US 7,151,175 B2
(45) Date of Patent: Dec. 19, 2006

(54) PROPENECARBOXYLIC ACID AMIDOXIME DERIVATIVES, A PROCESS FOR THE PREPARATION THEREOF, AND PHARMACEUTICAL COMPOSITIONS CONTAINING THE SAME

(75) Inventors: Peter Literati Nagy, Budapest (HU); Balazs Sumegi, Pecs (HU); Kalman Takacs, Budapest (HU)

(73) Assignee: N-Gene Research Laboratories Inc., New York, NY (US)

( * ) Notice: Subject to any disclaimer, the term of this patent is extended or adjusted under 35 U.S.C. 154(b) by 0 days.

(21) Appl. No.: 11/084,231

(22) Filed: Mar. 21, 2005

(65) Prior Publication Data

US 2005/0165019 A1 Jul. 28, 2005

Related U.S. Application Data

(62) Division of application No. 10/239,159, filed as application No. PCT/HU01/00029 on Mar. 13, 2001, now Pat. No. 6,887,872.

(30) Foreign Application Priority Data

Mar. 20, 2000 (HU) .................................... 0001178
Mar. 7, 2001 (HU) .................................... 0100987

(51) Int. Cl.
C07D 403/00 (2006.01)
C07D 413/00 (2006.01)
C07D 217/00 (2006.01)
C07D 215/38 (2006.01)
C07D 271/06 (2006.01)

(52) U.S. Cl. ...................... 540/603; 544/138; 546/147; 546/175; 546/210; 548/132

(58) Field of Classification Search .................... None
See application file for complete search history.

(56) References Cited

U.S. PATENT DOCUMENTS

| | | | |
|---|---|---|---|
| 4,308,399 A | 12/1981 | Takacs et al. | ................ 564/257 |
| 4,365,064 A | 12/1982 | Takacs et al. | ................ 546/148 |
| 4,430,270 A | 2/1984 | Preuss | ...................... 260/397.1 |
| 6,500,823 B1 | 12/2002 | Literati Nagy et al. | .. 514/231.5 |

FOREIGN PATENT DOCUMENTS

WO    WO 90/08131 A1    7/1990
WO    WO 00/14054 A1    3/2000

OTHER PUBLICATIONS

Pipik et al, "A Preferred Synthesis of 1,24-Oxadiazoles" Synthetic Communications, vol. 34(10), pp. 1863-1870 (2004).*

* cited by examiner

Primary Examiner—Zachary C. Tucker
(74) Attorney, Agent, or Firm—Birch, Stewart, Kolasch and Birch, LLP

(57) ABSTRACT

The invention refers to novel propenecarboxylic acid amidoxime derivatives furthermore N-oxides and/or geometrical isomers and/or optical isomers and/or pharmaceutically suitable acid addition salts and/or quaternary derivatives thereof. The novel compounds are suitable for the treatment of a state connected with oxygen deficit and/or energy deficit, or a disease based on PARP inhibition, especially an autoimmune or neurodegenerative disease, and/or a viral disease, and/or a disease caused by a toxic effect.

4 Claims, No Drawings

PROPENECARBOXYLIC ACID AMIDOXIME DERIVATIVES, A PROCESS FOR THE PREPARATION THEREOF, AND PHARMACEUTICAL COMPOSITIONS CONTAINING THE SAME

This application is a Divisional of application Ser. No. 10/239,159, filed on Nov. 20, 2002, now U.S. Pat. No. 6,887,872, which issued on May 3, 2005, and for which priority is claimed under 35 U.S.C. § 120; and this application claims priority of Application Nos. P0001178 filed in Hungary on Mar. 20, 2000 and P0100987 filed in Hungary on Mar. 7, 2001 under 35 U.S.C. § 119; the entire contents of all are hereby incorporated by reference. Application Ser. No. 10/239,159 is the national phase of PCT International Application No. PCT/HU01/00029 filed on Mar. 13, 2001 under 35 U.S.C. § 371.

FIELD OF THE INVENTION

The invention refers to novel propenecarboxylic acid amidoxime derivatives, a process for the preparation thereof, and pharmaceutical compositions containing the same. The novel compounds have valuable pharmaceutical effects, thus, they can be used especially in states connected with energy deficit of the cell, in oxygen deficient states of the heart and brain, in neurodegenerative diseases, in the treatment of autoimmune and/or viral diseases, furthermore in diseases caused by toxic effects.

BACKGROUND OF THE INVENTION

The preparation of some $\Delta^2$-1,2,4-oxadiazoline-5-one derivatives is described in the article Chem. Ber., 103, 2330–2335 (1970) without any reference to possible biological effects thereof. From the above compounds, the preparation of 5,6-dihydro-4H-1,2,4-oxadiazine derivatives is discussed in the article Chem. Ber., 108, 1911–1923 (1975), again without any reference to biological effects.

1,2,4-oxadiazoline-5-one derivatives having peripheral vasodilating, antianginal and antiarrhythmic effects are known from HU-P No. 179 951. 1,2,4-oxadiazine derivatives having peripheral vasodilating and blood pressure lowering, antiarrhythmic, slight antiphlogistic and diuretic effects are known from HU-P No. 180 708. However, the known 1,2,4-oxadiazoline-5-one and 1,2,4-oxadiazine derivatives do not contain any alkenyl substituents, i.e. they cannot be derived from a propenecarboxylic acid amidoxime.

The aim of the invention is to prepare novel compounds having valuable pharmaceutical effects.

SUMMARY OF THE INVENTION

It was found that the above aim is achieved by and, thus, the invention refers to the novel propenecarboxylic acid amidoxime derivatives of the formula

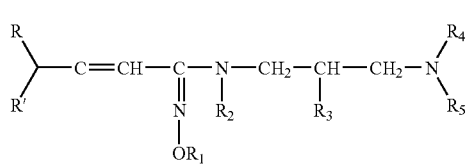

I wherein
R represents a $C_{1-20}$ alkyl group, a phenyl group which latter is optionally substituted by 1–3 substituent(s)—wherein the substituent is a halo atom and/or a $C_{1-2}$ alkyl group and/or a $C_{1-2}$ alkoxy group and/or an amino group and/or a ($C_{1-4}$ alkyl)amino group and/or a di($C_{1-4}$ alkyl)amino group and/or a ($C_{1-4}$ alkanoyl)amino group-, furthermore a 5- or 6-membered saturated or unsaturated heterocyclic group containing one or two nitrogen atom(s) or a sulphur atom as the heteroatom and said heterocyclic group is optionally fused with one or more benzene ring(s) and/or one or more heterocyclic group(s), and
R' stands for a hydrogen atom, or
R forms together with R' a $C_{5-7}$ cycloalkyl group optionally fused with a benzene ring,
$R_4$ and $R_5$ represent, independently, a hydrogen atom, a $C_{1-5}$ alkyl group, a $C_{-1-5}$ alkanoyl group or a phenyl group which latter is optionally substituted by 1–3 substituent(s)—wherein the substituent is a halo atom and/or a $C_{1-2}$ alkyl group and/or a $C_{1-2}$ alkoxy group-, or
$R_4$ and $R_5$ form together with the adjacent nitrogen atom a 5- or 6-membered saturated or unsaturated heterocyclic group that may contain a further nitrogen atom and/or an oxygen atom and/or a sulphur atom as the heteroatom and can be fused with a benzene ring, and the heterocyclic group and/or the benzene ring may bear one or two substituent(s) wherein the substituent is a halo atom and/or a $C_{1-2}$ alkyl group and/or a $C_{1-2}$ alkoxy group,
$R_1$ and $R_2$ stand for a hydrogen atom and
$R_3$ means a hydrogen atom, a hydroxy group or a $C_{1-5}$ alkoxy group, or
$R_1$ forms together with $R_2$ a carbonyl group or a thiocarbonyl group the carbon atom of which is bound to the oxygen atom adjacent to $R_1$ and to the nitrogen atom adjacent to $R_2$, and
$R_3$ represents a hydrogen atom, a halo atom, a hydroxy group, a $C_{1-5}$ alkoxy group, a $C_{1-5}$ alkylthio group, a $C_{1-20}$ alkanoyloxy group, a $C_{3-22}$ alkenoyloxy group containing one or more double bond(s), a methylsulfonyloxy group, a benzenesulfonyloxy group or a toluenesulfonyloxy group, or
$R_2$ is a hydrogen atom and
$R_1$ forms together with $R_3$ a valence bond between the oxygen atom adjacent to $R_1$ and the carbon atom adjacent to $R_3$, furthermore N-oxides or geometrical isomers and/or optical isomers and/or pharmaceutically suitable acid addition salts and/or quaternary derivatives thereof.

DESCRIPTION OF THE PREFERRED EMBODIMENTS

In the description and claims, under a $C_{1-20}$ alkyl group for example a methyl, ethyl, n-propyl, isopropyl, n-butyl, sec-butyl, tert.-butyl, isobutyl, n-pentyl, n-hexyl, n-heptyl, n-decyl, dodecyl, hexadecyl, octadecyl group etc. is meant.

A halo atom is, primarily, a fluoro, chloro or bromo atom, preferably a chloro or bromo atom.

A $C_{1-2}$ alkyl group is a methyl or ethyl group, while a $C_{1-2}$ alkoxy group is a methoxy or ethoxy group.

A $C_{1-4}$ alkyl group is a methyl, ethyl, n-propyl, isopropyl, n-butyl, sec-butyl, tert.-butyl or isobutyl group. A $C_{1-5}$ alkyl group can be, in addition to the ones listed above, e.g. a n-pentyl group, too.

A ($C_{1-4}$ alkyl)amino group is, for example, a methylamino, ethylamino, isopropylamino group etc. A di($C_{1-4}$ alkyl)amino group is, for example, a dimethylamino, diethylamino, methyl-isopropylamino group etc.

A $C_{1-4}$ alkanoyl group is, preferably, a formyl, acetyl, n-propionyl or n-butyryl group. A $C_{1-5}$ alkanoyl group can be, in addition to the ones listed above, e.g. a n-pentanoyl group, too.

A 5- or 6-membered saturated or unsaturated heterocyclic group containing one or two nitrogen atom(s) or a sulfur atom as the heteroatom is, for example, a pyrrolyl, pyratolyl, imidazolyl, thienyl, pyridyl, piperidyl, pirimidinyl, piperazinyl group etc.

A $C_{5-7}$ cycloalkyl group optionally fused with a benzene ring is, for example, a cyclopentyl, cyclohexyl, cycloheptyl, indanyl or tetralinyl group.

A 5- or 6-membered saturated or unsaturated heterocyclic group that may contain, in addition to the nitrogen atom adjacent to substituents $R_4$ and $R_5$, a further nitrogen atom and/or oxygen atom and/or sulfur atom as the heteroatom can be, in addition to the heterocyclic groups listed above, e.g. a morpholino group.

A $C_{1-20}$ alkanoyloxy group is, for example, a formyloxy, acetoxy, propionyloxy, butyryloxy, caproyloxy, palmitoyloxy, stearoyloxy group etc.

A $C_{3-22}$ alkenoyloxy group may contain, in general, 1–6 double bond(s), and is, preferably, a linolenoyloxy, linoleyloxy, docosahexaenoyloxy, eicosapentaenoyloxy or arachidonoyloxy group.

The pharmaceutically suitable acid addition salts of the propenecarboxylic acid amidoxime derivatives of the formula I and the N-oxides thereof are the acid addition salts formed with inorganic acids such as hydrochloric acid, sulfuric acid, phosphoric acid etc., or with organic acids such as acetic acid, fumaric acid, lactic acid, tartaric acid, succinic acid, malic acid, benzenesulfonic acid, p-toluenesulfonic acid etc.

In the quaternary derivatives of the compounds of the formula I and the N-oxides thereof, one or more nitrogen atom(s) of the propenecarboxylic acid amidoxime is quaternarized that is, for example, a further $C_{1-4}$ alkyl group or phenyl($C_{1-4}$ alkyl) group is bound to the nitrogen atom in question, thus, said nitrogen atom becomes of positive charge. Of the nitrogen atoms being present in the compound of the formula I, suitably the one adjacent to substituents $R_4$ and $R_5$ is quaternarized. If, in formula I, R represents a heterocyclic group containing a nitrogen atom such as a pyridyl group, the nitrogen atom of said heterocyclic group can be quaternarized, too.

In the N-oxides of the compounds of the formula I, one or more nitrogen atom(s) is/are present in oxidized form, thus, also an oxygen atom is bound to the nitrogen atom in question. Of the nitrogen atoms being present in the compound of the formula I, suitably the one adjacent to substituents $R_4$ and $R_5$ may be present as an N-oxide. If, in formula I, R represents a heterocyclic group containing a nitrogen atom such as a pyridyl group, the nitrogen atom of said heterocyclic group can be present as an N-oxide, too.

Due to the double bond present in formula I, the novel propenecarboxylic acid derivatives of the formula I as well as the N-oxides thereof may exist in the form of geometrical isomers i.e. cis or trans isomers or any mixtures thereof. The invention includes the pure geometrical isomers and any mixtures thereof.

In addition to geometric isomerism, certain compounds of the formula I as well as the N-oxides thereof contain one or more chiral carbon atom(s), consequently, these compounds may exist in the form of optical isomers, too. The invention includes also the pure optical isomers and any mixtures thereof.

A preferred subgroup of the compounds of the invention consists of the propenecarboxylic acid amidoxime derivatives of the formula

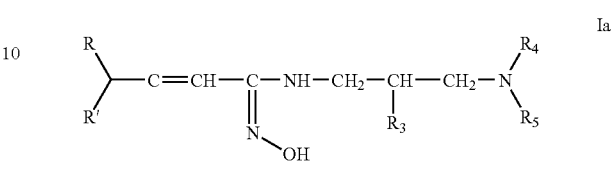

wherein $R_1$ and $R_2$ represent a hydrogen atom, $R_3$ stands for a hydrogen atom, a hydroxy group or a $C_{1-5}$ alkoxy group, R, R', $R_4$ and $R_5$ are as defined above, furthermore the N-oxides or geometrical isomers and/or optical isomers and/or pharmaceutically suitable acid addition salts and/or quaternary derivatives thereof.

Another preferred subgroup of the compounds of the invention consists of the oxadiazoline derivatives of the formula

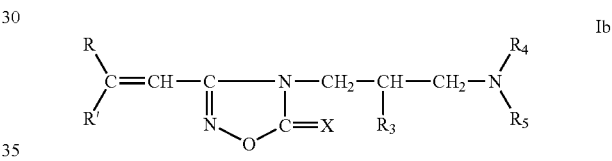

wherein $R_1$ forms together with $R_2$ a carbonyl group or a thiocarbonyl group the carbon atom of which is bound to the oxygen atom adjacent to $R_1$ and to the nitrogen atom adjacent to $R_2$, $R_3$ represents a hydrogen atom, a halo atom, a hydroxy group, a $C_{1-5}$ alkoxy group, a $C_{1-5}$ alkylthio group, a $C_{1-20}$ alkanoyloxy group, a $C_{3-22}$ alkenoyloxy group containing one or more double bonds, a methylsulfonyloxy group, a benzenesulfonyloxy group or a toluenesulfonyloxy group X stands for an oxygen atom or a sulfur atom, R, R', $R_4$ and $R_5$ are as defined in connection with formula I, furthermore the N-oxides or geometrical isomers and/or optical isomers and/or pharmaceutically suitable acid addition salts and/or quaternary derivatives thereof.

A further preferred subgroup of the compounds of the invention consists of the oxadiazine derivatives of the formula

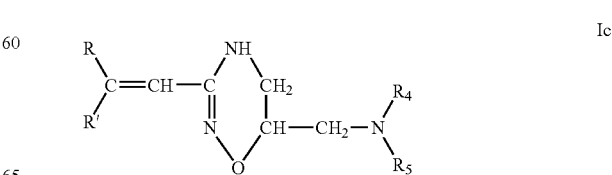

wherein
R$_2$ is a hydrogen atom and
R$_1$ forms together with R$_3$ a valence bond between the oxygen atom adjacent to R$_1$ and the carbon atom adjacent to R$_3$,
R, R', R$_4$ and R$_5$ are as defined in connection with formula I, furthermore the N-oxides or geometrical isomers and/or optical isomers and/or pharmaceutically suitable acid addition salts and/or quaternary derivatives thereof.

The propenecarboxylic acid amidoxime derivatives of the formula I are prepared as follows:

a) for the preparation of a propenecarboxylic acid amidoxime derivative of the formula Ia, wherein R$_1$, R$_2$ and R$_3$ represent a hydrogen atom, R, R', R$_4$ and R$_5$ are as defined in connection with formula I, a propene derivative of the formula

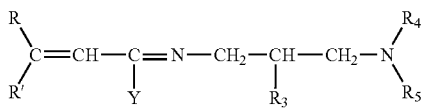
II wherein R, R', R$_3$, R$_4$ and R$_5$ are as defined above, Y stands for a halo atom or a group of the formula —SR$_6$, wherein R$_6$ means a hydrogen atom or a C$_{1-4}$ alkyl group, is reacted with hydroxylamine; or b) for the preparation of a propenecarboxylic acid amidoxime derivative of the formula Ia, wherein R$_1$ and R$_2$ represent a hydrogen atom, R$_3$ stands for a hydrogen atom or a hydroxy group, R, R', R$_4$ and R$_5$ are as defined in connection with formula I, an oxadiazoline derivative of the formula Ib, wherein R, R', R$_3$, R$_4$ and R$_5$ are as defined above, X stands for an oxygen atom or a sulfur atom, is reacted with an aqueous solution of an alkali hydroxide; or c) for the preparation of an oxadiazoline derivative of the formula Ib, wherein R$_3$ represents a hydrogen atom, X stands for an oxygen atom, R, R', R$_4$ and R$_5$ are as defined in connection with formula I, a Δ$^2$-1,2,4-oxadiazoline derivative of the formula

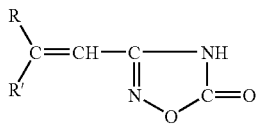
III wherein R and R' are as stated above, is reacted with an aminoalkyl halide of the formula

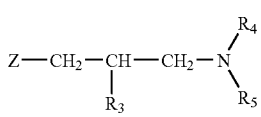
IV wherein Z means a halo atom, R$_3$, R$_4$ and R$_5$ are as stated above; or d) for the preparation of an oxadiazoline derivative of the formula Ib, wherein R$_3$ represents a hydrogen atom or a hydroxy group, X stands for an oxygen atom, R, R', R$_4$ and R$_5$ are as defined in connection with formula I, a Δ$^2$-1,2,4-oxadiazoline derivative of the formula III, wherein R and R' are as stated above, is reacted with a 1,3-dihalopropane of the formula

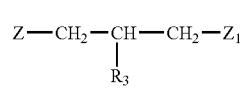
V wherein Z and Z$_1$ represent, independently, a halo atom, R$_3$ is as stated above, and the obtained Δ$^2$-1,2,4-oxadiazolinylalkyl halide of the formula

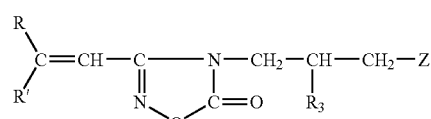
VI wherein R, R', R$_3$ and Z are as defined above, is reacted with an amine of the formula

VII wherein R$_4$ and R$_5$ are as defined above; or e) for the preparation of an oxadiazoline derivative of the formula Ib, wherein R$_3$ represents a hydroxy group, X stands for an oxygen atom, R, R', R$_4$ and R$_5$ are as defined in connection with formula I, a Δ$^2$-1,2,4-oxadiazoline derivative of the formula III, wherein R and R' are as stated above, is reacted with epichlorohydrin, and the formed Δ$^2$-1,2,4-oxadiazolinylalkyl chloride of the formula

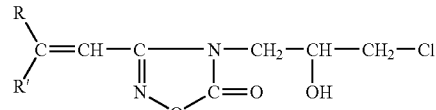
VIII wherein R and R' are as stated above, is reacted with an amine of the formula VII, wherein R$_4$ and R$_5$ are as defined above; or f) for the preparation of an oxadiazoline derivative of the formula Ib wherein R$_3$ represents a hydroxy group, X stands for an oxygen atom, R, R', R$_4$ and R$_5$ are as defined in connection with formula I, a Δ$^2$-1,2,4-oxadiazolinylalkyl chloride of the formula VIII, wherein R and R' are as stated above, is reacted with an acid binding agent, and the formed epoxide of the formula

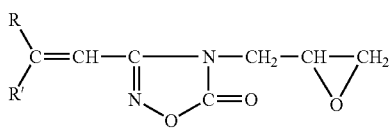

IX wherein R and R' are as stated above, is reacted with an amine of the formula VII, wherein $R_4$ and $R_5$ are as stated above; or g) for the preparation of an oxadiazoline derivative of the formula Ib wherein $R_3$ represents a hydrogen atom or a hydroxy group, X stands for an oxygen atom or a sulfur atom, R, R', $R_4$ and $R_5$ are as defined in connection with formula I, a propenecarboxylic acid amidoxime derivative of the formula Ia, wherein R, R', $R_3$, $R_4$ and $R_5$ are as defined above, is reacted with a carbonic acid derivative of the formula

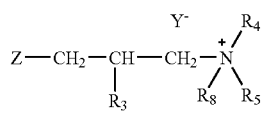

X wherein X is as defined above, $Z_2$ and $Z_3$ represent, independently, a halo atom, a $C_{1-4}$ alkoxy group or a $C_{1-4}$ alkylmercapto group; or h) for the preparation of an oxadiazine derivative of the formula Ic, wherein R, R', $R_4$ and $R_5$ are as defined in connection with formula I, an oxadiazoline derivative of the formula Ib wherein R, R', $R_4$ and $R_5$ are as stated above, X stands for an oxygen atom or a sulfur atom, $R_3$ means a halo atom, a methylsulfonyloxy group, a benzenesulfonyloxy group or a toluenesulfonyloxy group, is reacted with an alkali hydroxide in the presence of water; or i) for the preparation of an oxadiazine derivative of the formula Ic, wherein R, R', $R_4$ and $R_5$ are as defined in connection with formula I, a cyclic compound of the formula

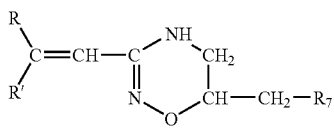

XI wherein R and R' are as defined above, $R_7$ stands for a halo atom, a methylsulfonyloxy group, a benzenesulfonyloxy group or a toluenesulfonyloxy group, is reacted with an amine of the formula VII, wherein $R_4$ and $R_5$ are as stated above; or j) for the preparation of a quaternary derivative of the formula

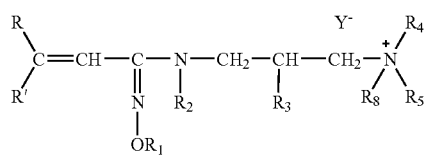

XII wherein R, R', $R_1$, $R_2$, $R_3$, $R_4$ and $R_5$ are as defined in connection with formula I, $R_8$ stands for a $C_{1-4}$ alkyl group or a phenyl($C_{1-4}$ alkyl) group, Y represents a halo atom or a group of the formula $R_8$—$SO_4$, wherein $R_8$ is as stated above, a $\Delta^2$-1,2,4-oxadiazoline derivative of the formula III, wherein R and R' are as stated above, is reacted with a quaternary alkyl halide of the formula

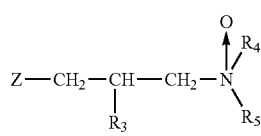

XIII wherein $R_3$, $R_4$, $R_5$, $R_8$ and Y are as stated above, Z represents a halo atom; or k) for the preparation of an N-oxide of the formula

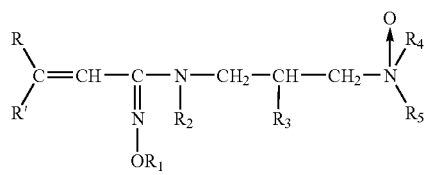

XIV wherein R, R', $R_1$, $R_2$, $R_3$, $R_4$ and $R_5$ are as defined in connection with formula I, a $\Delta^2$-1,2,4-oxadiazoline derivative of the formula III, wherein R and R' are as stated above, is reacted with a compound of the formula

XV wherein $R_3$, $R_4$ and $R_5$ are as stated above, Z stands for a halo atom; and if desired, an obtained compound of the formula Ib wherein $R_3$ represents a hydroxy group, R, R', $R_4$ and $R_5$ are as defined in connection with formula I, X stands for a oxygen atom or a sulfur atom, is reacted with a halogenating agent to obtain a compound of the formula Ib wherein $R_3$ is a halo atom; or if desired, an obtained compound of the formula Ib wherein $R_3$ represents a hydroxy group, R, R', $R_4$ and $R_5$ are as defined in connection with formula I, X stands for a oxygen atom or a sulfur atom, is reacted with a $C_{1-20}$ alkanecarboxylic halide or a $C_{3-22}$ alkenecarboxylic halide containing one or more double bond(s) to obtain a compound of the formula Ib wherein $R_3$ stands for a $C_{1-20}$ alkanoyloxy group or a $C_{3-22}$ alkenoyloxy group; or if desired, an obtained compound of the formula Ib wherein $R_3$ represents a hydroxy group, R, R', $R_4$ and $R_5$ are as defined in connection with formula I, X stands for a oxygen atom or a sulfur atom, is reacted with a $C_{1-5}$ alkyl halide to obtain a compound of the formula Ib wherein $R_3$ represents a $C_{1-5}$ alkoxy group; or if desired, an obtained compound of the formula Ib wherein $R_3$ represents a halo atom, R, R', $R_4$ and $R_5$ are as defined in connection with formula I, X stands for a oxygen atom or a sulfur atom, is reacted with an alkali salt of a $C_{1-5}$ alkanol or a $C_{1-5}$ thioalkanol to obtain a compound of the formula Ib wherein $R_3$ means a $C_{1-5}$ alkoxy group or a $C_{1-5}$ alkylthio group; or if desired, an obtained compound of the formula Ib wherein $R_3$ represents a hydroxy group, R, R', $R_4$ and $R_5$ are as defined in connection with formula I, X stands for a oxygen atom or a sulfur atom, is reacted with a methylsulfonyl halide, a benzenesulfonyl halide or a toluenesulfonyl halide to obtain a compound of the formula Ib wherein $R_3$ represents a methylsulfonyloxy group, a benzenesulfonyloxy group or a toluenesulfonyloxy group; and if desired, and obtained compound of the formula I is reacted with an inorganic or organic acid to obtain a pharmaceutically suitable acid addition salt, or the base is set free from the acid addition salt thereof, and/or one or more nitrogen atom(s) of a compound of the formula I is quaternarized with an alkylating agent, and/or a compound of the formula I is reacted with an oxidizing agent to convert one or more nitrogen atom(s) thereof to N-oxide.

In process a) of the invention, the reaction of the propene derivative of the formula II with hydroxylamine is carried out in a solvent or in a mixture of solvents using hydroxylamine base that can be set free also in situ from an acid addition salt thereof by the addition of a strong base. The formed product of the formula Ia is separated in a manner known per se, for example, by crystallization from the reaction mixture or by evaporation of the reaction mixture or by precipitation of the acid addition salt thereof.

If a propene derivative of the formula II, wherein Y stands for a halo atom, is used, the solvent is an anhydrous indifferent organic solvent e.g. a halogenated hydrocarbon such as chloroform, dichloromethane etc., a hydrocarbon such as benzene, toluene etc. or any other solvent usually employed in acylation reactions such as pyridin.

If a propene derivative of the formula II, wherein Y stands for a group of the formula —$SR_6$, is used, in addition to the types of solvent listed above e.g. also alkanols can be employed as the organic solvent.

The propene derivative of the formula II, wherein Y represents a halo atom, generally a chloro atom,—as a matter of fact, said compound is an imidoyl halide, generally an imidoyl chloride—is prepared from the corresponding acid amide of the formula

XVI

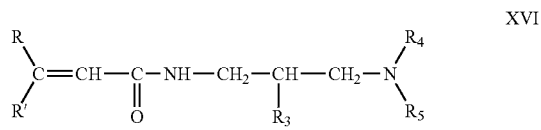

wherein R, R', $R_4$ and $R_5$ are as defined in connection with formula I, $R_3$ stands for a hydrogen atom or a $C_{1-5}$ alkoxy group, by reaction with a halogenating agent, suitably thionyl chloride, phosphorus trichloride, phosphorus pentachloride etc. in a manner known from the literature.

The propene derivative of the formula II, wherein Y represents a mercapto group, can be prepared, for example, from the corresponding acid amide of the formula XVI with phosphorus pentasulfide in an organic solvent such as toluene, xylene or pyridine in a manner known from the literature. The propene derivative of the formula II, wherein Y stands for an alkylthio group, is obtained by reacting the propene derivative of the formula II, wherein Y means a mercapto group, with an alkylating agent.

In process b) of the invention, the oxadiazoline ring is opened by using the process known from Chem. Ber., 103, 2330–2335 (1970) which consists of an alkaline hydrolysis in aqueous medium. As the alkali hydroxide, suitably potassium hydroxide or sodium hydroxide is used, to the aqueous solution of which, if desired, an organic solvent, preferably an aliphatic alcohol such as methanol or ethanol is added, too. In the process of the invention, the oxadiazoline ring is opened at the boiling point of the reaction mixture in a short time and the compound of the formula Ia is obtained with a good yield. The reaction product can be separated in a manner known per se as described in connection with process a).

In process c) of the invention, the reaction is carried out in an organic solvent that is indifferent from the point of view of the reaction, in the presence of an acid binding agent, in general, at the boiling point of the reaction mixture. The indifferent organic solvent is, for example, an alkanol such as methanol or ethanol, a hydrocarbon such as benzene, toluene or xylene or a mixture thereof. As the acid binding agent, inorganic or organic bases can be used. The reaction mixture can be worked up by the usual methods, for example, the solvent is evaporated and the product is crystallized or the acid addition salt thereof is precipitated.

The $\Delta^2$-1,2,4-oxadiazoline derivatives of the formula III can be prepared from the corresponding amidoximes by reaction with carbonic acid derivatives. Some representatives of the amidoximes are known from the article Chem. Rews., 62, 155 (1962). The novel amidoximes can be prepared from the corresponding propenecarboxylic nitrile by reaction with hydroxylamine in a manner described in the article. Most of the aminoalkyl halides of the formula IV are known compounds which are either commercially available or can be prepared in a simple way by reacting an 1,3-dihalopropane with an amine of the formula VII.

In process d) of the invention, both the alkylation—i.e. the reaction of a $\Delta^2$-1,2,4-oxadiazoline derivative of the formula III with a 1,3-dihalopropane of the formula V—and amination—i.e. the reaction of a formed $\Delta^2$-1,2,4-oxadiazolinylalkyl halide of the formula VI with an amine of the formula VII—are carried out in an organic solvent that is indifferent from the point of view of the reaction, in the presence of an acid binding agent, suitably an inorganic base such as sodium hydroxide or sodium carbonate, generally at the boiling point of the reaction mixture. The $\Delta^2$-1,2,4-oxadiazolinylalkyl halide of the formula VI that forms during the alkylation is either crystallized or used, after the evaporation of the reaction mixture, without crystallization, for the amination reaction. The formed reaction product of the formula Ib is separated in a manner known per se using any of the methods described above. The indifferent organic solvent can be a hydrocarbon or a halogenated aliphatic or aromatic hydrocarbon such as chloroform, an alkanol such as methanol or ethanol, a ketone such as acetone or a mixture of the types of solvent listed.

In process e) of the invention, the reaction of the $\Delta^2$-1,2,4-oxadiazoline derivative of the formula III with epichlorohydrin is performed in an organic solvent that is indifferent from the point of view of the reaction or in the absence of any solvent, preferably in an excess of epichlorohydrin, suitably at the boiling point of the reaction mixture. The indifferent organic solvent can be, for example, a hydrocarbon, an ether such as dioxane, tetrahydrofuran etc. Bases such as sodium hydroxide, sodium carbonate etc. are used as the catalyst. After the end of the reaction, the solvent is evaporated and the residue is crystallized. The formed $\Delta^2$-1,2,4-oxadiazolinylalkyl chloride of the formula VIII is reacted with the amine of the formula VII in a similar manner as described under the amination reaction in process d). The formed reaction product of the formula Ib is separated in a manner known per se using any of the methods described above.

In process f) of the invention, the acid binding agent is, for example, an alkali carbonate such as sodium carbonate, potassium carbonate etc. or an alkali hydroxide such as sodium hydroxide, potassium hydroxide etc. for the preparation of the epoxide of the formula IX. The reaction is carried out in an organic solvent that is indifferent from the point of view of the reaction, suitably at the boiling point of the reaction mixture. As the indifferent organic solvent, for example, a hydrocarbon, acetone, an ether such as tetrahydrofuran or dioxane, a halogenated aliphatic or aromatic hydrocarbon etc. is used. The reaction mixture is filtered, the filtrate is evaporated, and the formed epoxide of the formula IX is crystallized, then reacted with the amine of the formula VII in a manner described in process d) in connection with the amination, preferably in an alkanol. As an alternative procedure, the epoxide of the formula IX is not separated but the amine of the formula VII is added directly to the reaction mixture in which the epoxide has been prepared, and the reaction mixture is heated further. The formed reaction product of the formula Ib is separated in a manner known per se using any of the methods described above.

In process g) of the invention, any carbonic acid or thiocarbonic acid derivative of the formula X can be used for the ring closure reaction which reagent is capable of forming a carbonyl or thiocarbonyl group, respectively, between the oxygen atom of the hydroxy group and the nitrogen atom of the amino group in case of the part having the formula —C(=N—OH)—NH— in formula Ia. Suitable compounds include the carbonic acid and thiocarbonic acid halides such as phosgene and thiophosgene, halide esters such as ethyl chloroformate or alkyl chlorothioformates, or esters such as dialkyl carbonates, mono-, di- and trithiocarbonates, xanthogenates etc. An organic solvent that is indifferent from the point of view of the reaction is used for the ring closure reaction, however, the reaction can be carried out in the absence of any solvent, too. The reaction mixture is cooled or heated, suitably the ring closure is performed at the boiling point of the reaction mixture. The formed reaction product of the formula Ib is separated in a manner known per se using any of the methods described above.

If a carbonic acid of the formula X, wherein one or both of $Z_2$ and $Z_3$ represent(s) a halo atom, is used for the reaction, then suitably a hydrocarbon, a halogenated aliphatic or aromatic hydrocarbon or an ether is employed as the indifferent organic solvent. If both $Z_2$ and $Z_3$ stand for an alkoxy or alkylmercapto group, then the indifferent organic solvent can be, in addition to the ones listed, alkanol, too.

In process h) of the invention, as a matter of fact, the oxadiazoline ring is transformed into an oxadiazine ring. For this purpose the method known from Chem. Ber., 108, 1911–1923 (1975) is used. Suitably, sodium hydroxide or potassium hydroxide is employed as the alkali hydroxide. The reaction is carried out in the mixture of an organic solvent such as an alkanol and an aqueous solution of an alkali hydroxide at the boiling point of the reaction mixture. The formed reaction product of the formula Ic is separated in a manner known per se using any of the methods described above.

In process i) of the invention, the reaction is performed in an organic solvent that is indifferent from the point of view of the reaction or in a mixture of several such solvents, in the presence or absence of an acid binding agent. The indifferent organic solvent is, for example, a hydrocarbon, a halogenated aliphatic or aromatic hydrocarbon, an ether or an alkanol, preferably butanol. The reaction can be carried out also in the absence of any organic solvent, in this case an excess of the amine of the formula VII can be used as the solvent. The formed reaction product of the formula Ic is separated in a manner known per se using any of the methods described above.

In processes j) and k) of the invention, the procedure is similar to the one described in process c). The quaternary alkyl halide of the formula XIII is prepared by quaternarizing the corresponding aminoalkyl halide of the formula IV. The compound of the formula XV can be prepared from the corresponding aminoalkyl halide of the formula IV with an oxidizing agent.

An oxadiazoline derivative of the formula Ib wherein $R_3$ stands for a hydroxy group, can be converted to the corresponding compound of the formula Ib wherein $R_3$ represents a halo atom, by reaction with a halogenating agent. Preferably thionyl chloride, phosphorus trichloride or phosphorus pentachloride is used as the halogenating agent, and the halogenation is carried out in organic solvents usually employed in similar reactions or in the absence of any solvent, for example in an excess of the halogenating agent. The reaction mixture is worked up by the methods usually employed after halogenation reactions.

An oxadiazoline derivative of the formula Ib wherein $R_3$ stands for a hydroxy group, can be reacted with an active acylating derivative of a $C_{1-20}$ alkanecarboxylic acid or a $C_{3-22}$ alkenecarboxylic acid such as a halide, anhydride, azide etc., or with a methylsulfonyl halide, benzenesulfonyl halide or toluenesulfonyl halide in an indifferent organic solvent, preferably an aromatic hydrocarbon or a halogenated aromatic or aliphatic hydrocarbon, in the presence or absence of an acid binding agent. The corresponding reaction product of the formula Ib that forms can be separated by the usual methods described above.

A compound of the formula Ib wherein $R_3$ represents a hydroxy group, can be reacted with a $C_{1-5}$ alkyl halide in a similar way. In this case, one or more nitrogen atom(s) of the compound can be quaternarized simultaneously.

The reaction of a compound of the formula Ib wherein $R_3$ stands for a halo atom, preferably a chloro atom, with the alkali salt of an alkanol or thioalkanol can be performed under the reaction terms described above.

If desired, a compound of the formula I is converted to a pharmaceutically suitable acid addition salt or set free from the acid addition salt thereof. If, in the salt formation, an optically active organic acid, for example, camphoric acid, camphorsulfonic acid, tartaric acid or tartaric acid derivative is used, the separation of the stereoisomers of the compounds having a chiral centre becomes possible. In this case, the resolution is carried out in a manner known per se by the fractionated crystallization of the acid addition salts formed with the optically active organic acid.

If desired, one or more nitrogen atom(s) of a propenecarboxylic acid amidoxime derivative of the formula I is quaternarized. For this purpose, the compound of the formula I is reacted with an alkylating agent of the formula $R_8$—Y, wherein $R_8$ represents a $C_{1-4}$ alkyl group or a phenyl($C_{1-4}$ alkyl) group, Y stands for a halo atom, to obtain a quaternary derivative of the formula XII, wherein $R_8$ and Y are as stated above. The quaternarization reaction can be also carried out with a dialkyl sulfate of the formula $(R_8)_2 SO_4$, wherein $R_8$ is as stated above. In the latter case a quaternary derivative of the formula XII, wherein Y means a group of the formula $R_8$—$SO_4$, is obtained. The quaternarization reaction is performed in an indifferent organic solvent or in the absence of any solvent.

Alternatively, another nitrogen atom or a further nitrogen atom of the compound of the formula I can be quaternarized, too. If, in formula I, R represents a heterocyclic group containing a nitrogen atom, for example, a pyridyl group, the nitrogen atom of the pyridyl group can be quaternarized or this nitrogen atom can be also quaternarized.

When a compound of the formula I is converted to an N-oxide, suitably the nitrogen atom is oxidized to which the substituents $R_4$ and $R_5$ are bound. In this case, oxidization is performed, in general, with hydrogen peroxide, preferably in a solution containing an alkanol such as methanol, suitably at room temperature. If, in formula I, R represents a heterocyclic group containing a nitrogen atom, for example, a pyridyl group, the nitrogen atom of the pyridyl group can be simultaneously or instead of the above nitrogen atom converted to N-oxide with an oxidizing agent. In this case, the oxidizing agent is, preferably, a peroxy acid e.g. 3-chloroperbenzoic acid, and the oxidization reaction is carried out in an indifferent organic solvent, generally an aromatic hydrocarbon such as benzene or toluene, suitably at room temperature.

Of course, an N-oxide of the compound of the formula I can be also converted to a pharmaceutically suitable acid addition salt or a quaternary derivative thereof in a manner known per se.

The pharmacological effect of the compounds of the invention is determined by the following tests.

Examination of PARP Inhibition

It is known that reactive oxygen species (ROS) e.g. hydroxy radical, superoxide, peroxynitrite, hydrogen peroxide form continuously in the living organism [Richter, C., FEBS Lett., 241, 1–5 (1988)] and in low quantity they play a role in controlling important physiological processes [Beck, K. F. et al., J. Exp. Biol., 202, 645–53 (1999); McDonald, L. J. and Murad, F., Proc. Soc. Exp. Biol. Med., 211, 1–6 (1966)] (such as angiectasis, platelet aggregation, leukocyte adhesion). The concentration of reactive oxygen species and nitrogen oxide is significantly higher in acute and chronic inflammations, for example in the majority of autoimmune diseases [Taraza, C. et al., Rom. J. Intern. Med., 35, 89–98 (1997)], in case of postischemic heart failure, ischemic brain (stroke) [Brain Pathology, 9, 119–131 (1999)]. The source of the ROS includes the normal tissue cells due to, partly, the leukocytes and macrophages present in the inflamed tissue, partly, the inductive effect of the inflammatory cytokines.

The reactive oxygen species injure, among others, the DNA. A complex defensive and repair process is initiated in the cell by the damage of DNA. An important element of this process is the activation of the enzyme poly(adenosine diphosphate ribose)-polymerase (PARP). PARP is an enzyme of nuclear arrangement which is present in nearly every cell in large amount and catalyzes the transport of the adenosine diphosphate ribose unit from nicotinic acid adenine dinucleotide (NAD) to proteins and the build-up of poly(adenosine diphosphate ribose) chains. The main substrates of the enzyme includes itself [Gonzalez, R. et al., Mol. Cell. Biochem., 138, 33–37 (1994)], nuclear proteins, histones, topoisomerase I and II, transcription factors. The activity of the PARP enzyme is enhanced by a factor of about 500 in case of a break in the DNA chain [Menissier de Murcia, J. et al., J. Mol. Biol., 210, 229–233 (1989)]. A critical lowering of the NAD concentration is caused by PARP enzyme activation owing to an extreme high DNA damage. As a consequence, the synthesis of adenosine triphosphate (ATP) is reduced in the cell and, at the same time, the use of ATP becomes higher since the cell tries to restore the NAD level from adenosine diphosphate ribose and nicotinic amide by using ATP. These biochemical processes damage the important in the therapy of several diseases such as autoimmune clinical patterns [Szabó, C. et al., Trends Pharmacol. Sci., 19, 287–98 (1998)], the ischemic states of the heart and the brain as well as neurodegenerative diseases. NAD catabolism can be eliminated by the inhibition of the PARP enzyme, thus, reducing the nicotinic amide and adenosine diphosphate ribose levels in the cells and inhibiting the consumption of adenosine trophosphate for the NAD synthesis; that is to say, the above mentioned damage and death of the cells can be eliminated by the enzyme inhibition.

Determination of PARP Inhibition, In Vitro, on Isolated Enzyme

The poly(adenosine diphosphate ribose)polymerase was isolated from rat liver according to the article of Shah, G. M. [Anal. Biochem., 227, 1–13 (1995)]. The PARP activity was determined in 130 µl of reaction mixture consisting of 100 mM of tris-HCl buffer, pH 8.0, 10 mM of $MgCl_2$, 10% glycerol, 1.5 mM of DTT, 100 µg of (32P) or (3H) NAD+, 10 µg of activated DNA, 10 µg of histone. [Tris-HCl is tris(hydroxymethyl)aminomethane hydrochloride.] After 10 minutes of incubation time, the reaction was stopped with 8% perchloric acid, and the protein was separated through centrifugation (10 minutes, 10.000×g). The precipitate was washed with 8% perchloric acid three times, and the radioactivity bound to the protein was measured with a scintillation counter. The results can be seen in Table I.

TABLE I

| Compound (Example No.) | PARP $I_{0.5}$ in mg/l |
|---|---|
| 2 | 9 ± 2 |
| 3 | 8 ± 1 |
| 4 | 14 ± 2 |
| 5 | 13 ± 2 |
| 6 | 17 ± 3 |
| 8 | 12 ± 2 |
| 9 | 7 ± 1 |
| 10 | 28 ± 4 |
| 12 | 18 ± 3 |
| 13 | 20 ± 3 |
| 14 | 9 ± 2 |
| 16 | 18 ± 3 |

The above data are given from four parallel measurements. It can be seen in Table I that a part of the compounds tested is a very good PARP inhibitor ($I_{0.5}$<10 mg/l). A bigger part of the compounds tested can be classified as good PARP inhibitor ($I_{0.5}$=10–28 mg/l).

Effect of the Compounds of the Formula I on Heart Ischemic Failure and Reperfusion Arrhythmia The cardiac muscle damage and the cardiac muscle-cell death occurs, in the majority of cases, through feeding disorders. The most common form of feeding disorder is lack of oxygen. The cardiac muscle damage that develops is the cardiac muscle ischemia which can be formed through acute hypoxia/anoxia, coronary occlusion, spasmus or chronic coronary disease. The ischemic part of acute cardiac muscle infarction is followed by an excess bloodstream phase, the so called reperfusion phase. As a fatal consequence of reperfusion, arrhythmias (implicated ventricular tachycardia and fibrillation) may occur. These are the first manifestations of reperfusion injury. The prevention of reperfusion cardiac muscle disorder by drug administration means the prevention of the mortal danger of early post-infarction.

Experiments were carried out in male SPRD rats (acceptable body weight range: 300–350 g). The animals were anesthetized by the administration of pentobarbital [5-ethyl-5-(1-methylbutyl)-2,4,6-(1H,3H,5H)-pyrimidintrione] (60 mg/kg intraperitoneally), and remained breathing spontaneously. The animals were ventilated with a respirator (manufactured by Kutesz, Hungarian Academy of Sciences) by using a trachea cannule inserted after tracheotomy. The standard lead of the ECG II was monitored. The right femoral artery was catheterized and connected to a pressure transducer (BPR-01, Experimetria, Hungary) and a preamplifier. The pulsotachometer (HG-M, Experimetria, Hungary) was started by the pulsating signal of arterial blood pressure. The external jugular vein was cannulated for drug administration. After thoracotomy, a silk (braided, coated 4-0) was placed under the left anterior coronary (LAD) artery. After a few minutes' stabilization period, a 5 min occlusion of LAD artery was applied followed by a 10 min reperfusion period. ECG was recorded in the normal state at the start and in the above periods. From the data of ECG, the span of time of ventricular tachycardia and fibrillation was determined in sec. In addition, the survival ratios in the treated animal groups were recorded.

The results obtained indicate that the compounds of the invention are suitable for the prevention of the reperfusion-induced arrhythmia. For example, the animals treated with the compound of Example 2 have shown longer survival by 50% relative to the control group after reperfusion.

Examination of the Compounds of the Formula I in Global Cerebral Ischemia

After a human ischemic insult, the pyramidal cells of the hippocampus CA1 region are destroyed for the most part, the other cells of the region (CA2, CA3) are not so sensitive [Crain, B. J. et al.: Selective neuronal death after transient forebrain ischemia in the Mongolian gerbil, a silver impregnation study. Neuroscience, 27, 402 (1988)]. According to some authors, the disturbances of memory are connected with the death of the hippocampus cells [Walker, A. E. et al.: The national survey of stroke NINCDS, NIH: Clinical findings, Stroke, 12, Suppl., 1, 1–44 (1981)]. The central nervous system of mammals is not equally sensitive to the ischemic injury. The Mongolian gerbil (Meriones unguiculatus) is—owing to the anatomical faculty thereof—rather suitable for the examination of the cerebral ischemia since in this species 90% of the basilar anastomosis system (Circulus Willisi) fails, thus, there is no connection between the carotid artery and vertebral artery systems. Thus, extensive forebrain ischemia can be induced by pressing the carotid.

The aim of the test is to determine whether the novel compounds of the formula I possess a protective effect in global cerebral ischemia. The experiments were carried out in male Mongolian gerbils. The animals were anesthetized with a mixture of 2% of halothane [2-bromo-2-chloro-1,1,1-trifluoroethane], 68% of nitrogen oxide and 30% of oxygen. In the anesthesia, the carotid was pressed on both sides for 5 minutes. The neurons are not destroyed at once, therefore four days of reperfusion period followed the pressing (cell death of late type). On the fourth day after the intervention, 80–90% of the cells were damaged in the CA1 pyramidal region.

In order to determine the learning and memory abilities as well as the hypermotility, the animals were tested in an Y-labyrinth.

The cell death of the CA1 region was studied on histological sections. The animals were perfused with buffered formaldehyde, the brain was removed and fixed in formaldehyde. The growth of the destroyed CA1 areas were determined on the brain sections after staining.

The following materials were used for the tests:
GYKI-52466 (reference material) in a dose of 40 mg/kg i.p., administered 30 minutes after ischemia;
nimodipine [1,4-dihydro-2,6-dimethyl-4-(3-nitrophenyl)-3,5-pyridinedicarboxylic acid 2-methoxyethyl 1-methylethyl ester] (reference material) in a dose of 10 mg/kg i.p., administered 5 and 30 minutes after ischemia;
novel compound of the formula I in a dose of 25 mg/kg i.p., administered 5 and 30 minutes after ischemia.
Test groups:
ischemic control,
treated with a reference material after ischemia,
treated with a test material after ischemia,
pseudo-operation.

In the Tests it could be established that the compounds of the formula I have a protective effect in global cerebral ischemia.

The Effect of the Compounds of the Formula I Against Autoimmune Diseases

An autoimmune disease is an illness in which an immune reaction is started by the organism against a normal constituent thereof [Ring, G. H. et al., Semin. Nephrol., 19, 25–33 (1999); Theofilopoulos, A. N., Ann. N.Y. Acad. Sci., 841, 225–235 (1998)]. The various autoimmune diseases differ from each other in the antigene that starts the process, however, a great similarity can be established in the cell tissue destroying mechanism of the autoimmune process developed [Szabó, C. et al., Proc. Natl. Acad. Sci. USA, 95, 3867–3872 (1998)]. The autoimmune diseases include, in the first place, the following ones:
hormonal diseases: insulin dependent diabetes mellitus (IDDM);
liver diseases: hepatitis;
skin diseases: bullous pemphigoid lupus, pemphigus vulgaris, psoriasis, scleroderma, vitiligo;
diseases of the blood forming organ: sarcoidosis;
arthopathies: rheumatoid arthritis;
vascular diseases: vasculitis, takayasu arteritis, polyarteritis nodosa, ankylosing spondylitis;
intestinal diseases: colitis ulcerosa;
diseases of the muscular and nervous system: sclerosis multiplex, myasthenia gravis, chronic inflammatory demyelinating polyneuropathy.

Of the autoimmune diseases listed the prevention of the streptozotocin-induced type I diabetes mellitus was investigated on mice.

Insuline, the main regulator of the carbohydrate metabolism in the body, is produced and transferred to the blood stream by the cells of the Langerhans islet of the pancreas.

Damage or desctruction of the β-cells causes the decrease or cease of insulin production which leads to the development of the type I diabetes mellitus. β-cells are especially sensitive to ROS and to the toxic effects of nitrogen oxide. The study of DNA damage caused by nitrogen oxide led to the assumption that the excessive activation of the PARP enzyme and the decrease of NAD level are responsible for the death of β-cells [Heller, B. et al., J. Biol. Chem., 270, 11176–180 (1995)]. With a similar mechanism, streptozotocin (SZ) [2-deoxy-2-(3-methyl-3-nitrosoureido)-D-glucopyranose] is damaging the insulin producing β-cells, thus, offering a model of the type I diabetes when used in animal experiments [Yamamoto, H. et al., Nature, 294, 284–286 (1981)]. DNA is damaged by streptozocin through alkylation and formation of nitrogen oxide which causes activation of the PARP enzyme as mentioned above. It was examined whether the blood glucose level enhancing effect of a single dose of streptozotocin in mice could be prevented by a single dose of the propenecarboxylic acid amidoxime derivatives of the formula I. The experiments were carried out on CD-1 male mice. The animals were divided into three groups each of which consisting of 8 animals. The first group received 160 mg/kg of streptozotocin (Sigma) i.p., the second group received 160 mg/kg of streptozotocin and 200 mg/kg of the compound of the formula I p.o., the third group served as the control. The blood glucose concentration was determined on the third day after the treatment. Then, the animals were killed, and serum samples were taken for insulin determination.

It was found that the tested compound of the invention reduced significantly the blood glucose level enhanced by the addition of streptozotocin.

Effect Against Insulin Resistance

The type II diabetes mellitus is not insulin dependent. The essentiel of the pathomechanism of this latter type is the decrease or loss of insulin sensitivity of peripheral tissues, especially in striated (skeletal) muscles and adipose tissue. Naturally, this insensitivity cannot be compensated by overproduction (hypersecretion) of the Langerhans islet beta cells. It is important to stress that the insulin resistance, even without the onset of a real diabetes mellitus, leads to several cardiovascular regulatory disorders. Hence, the insulin resistance is the independent risk factor of the coronary vascular disease. Due to central pathophysiological importance of insulin resistance, the pharmacotherapic possibilities aiming at the increase of insulin sensitivity are very important in the drug research. The only really insulin sensitizer drugs in the clinical practice are the so-called thiazolidinediones. Their toxicity (which is mainly hepatotoxicity) is a limiting factor in their use. Insulin sensitizers decrease blood levels of glucose, triglycerides and insulin through a mechanism that involves increased insulin sensitivity in the target tissues (liver, skeletal muscles, adipocytes) [Colca, J. R., and Morton, D. R.: Antihyperglycamic thiazolidines: Ciglitazone and its analogues, in New Antidiabetic Drugs, edited by Bailey, C. J. and Flatt, P. R., Smith-Gordon, New York, 1990, pp. 255–261].

It was investigated whether treatment with the compounds of the invention effected insulin sensitivity of normal and hypercholesterolaemic conscious rabbits. Adult male white New Zealand rabbits weighing 3–3.5 kg, housed in an animal room (12-hour light/dark periods a day, temperature of 22–25° C., humidity of 50–70%), fed commercial laboratory chow and tap water ad libitum were used throughout. The experimental period commenced after a two-week adaptation period. The rabbits were randomized into two main groups. Half of the animals were continued to feed normal rabbit chow, whereas the second group animals were fed chow enriched with 1.5% cholesterol over a period of eight week. Each main group was divided into four treatment groups:

untreated group, group treated with a compound of the invention, 10 mg/kg i.v. dose twice a day over 4 days, group treated with 7-nitroindazole as NOS inhibitor: administration of 5 mg/kg of 7-nitroindazole over 5 min. preceded insulin administration with a 5-min inter-infusion interval, group treated with both 7-nitroindazole and the compound of the invention as described.

The animals were anaesthetized and polyethylene catheters were inserted into two major branches of the right jugular vein and the left carotid artery. The catheters were exteriorized through the back of the neck and filled with physiological saline containing heparin.

Studies on Isolated Vessel

From the thoracic aorta and carotid arterics of rabbits, vessel rings of 4 mm length were prepared and mounted horizontally on two small L-shaped glass hooks of which one was connected to a force transducer (SG-02, Experimetria, London, UK) for measurement and recording of isometric tension. The experiments were carried out in an organ chamber (5 ml) filled with Krebs solution gassed with 95% of oxygen and 5% of carbon dioxide. The initial resting tension was set at 20 and 10 mN for the aorta and carotid rings, respectively. The equilibration time amounted to 60 minutes. Subsequently, the vessel rings were exposed to increasing concentrations of noradrenaline in a cumulative manner. After the maximum response, the noradrenaline was washed out from the organ chamber until tension returned to the previous baseline level. To study vascular reactivity to acetylcholine, the rings were precontracted by the $EC_{50}$ concentration of noradrenaline. After a suitable contraction was obtained, the preparations were exposed to cumulative increases in acetylcholine chloride.

In a second set of vascular reactivity studies, a separate group of carotid artery rings were subjected to electrical field stimulation. After an initial tension set of 10 mN, the rings were allowed to equilibrate over 1 hour. Contractile responses to two consecutive trains of impulses of electrical field stimulation (100 stimuli, 20 V, 0.1 ms and 20 Hz) were then studied. The field stimulation protocol was then repeated in the presence of 1 μM of atropine and 4 μM of guanethidine ("non-adrenergic non-cholinergic=NANC solution). The whole protocol was accomplished with rings with intact endothelium and with those from which the endothelial layer had been gently removed.

Determination of tissue cyclic GMP (guanyl monophosphate) content according to Szilvássy [Szilvássy, Z. et al., Coron art. Dis., 4, 443/452 (1993); Am. J. Physiol., 266, H2033–H2041 (1994)]:

The muscle rings were instantly frozen with the use of a prechilled Wollenberger clamp and pulverized in liquid nitrogen. The samples were then homogenized in 6% (v/v) trichloroacetic acid of 10 times higher quantity than sample weight in a mortar previously kept at −70° C. After thawing, the samples were processed at 4° C. Sedimentation at 15,000 g for 10 min by means of a Janetzki K-24 centrifuge (Leipzig, Germany) was followed by extraction of the supernatant with 5 ml of water-saturated ether in a Wortex extractor over 5 min. The ether fraction was eliminated and the extraction was then five times repeated. Then the samples were evaporated under nitrogen and assayed for cyclic GMP contents by use of Amersham radioimmunoassay kits. Values are expressed as pmol/mg wet tissue weight.

Hyperinsulinaemic euglycaemic clamp studies: Human regular insulin was infused at a constant rate (13 mU/kg) via one of the venous cannula over 120 min. This insulin infusion rate yielded plasma insulin immunoreactivity of 100±5 µM/ml in the steady state. Blood samples (0.3 ml) were taken from the arterial cannula for blood glucose concentration at 10 min intervals. Blood glucose concentration was maintained constant (5.5±0.5 mmole/l) by a variable rate of glucose infusion via the second venous cannula. When blood glucose stabilized for at least 30 min, we defined this condition as steady state, and additional blood samples (0.5 ml) were taken for plasma insulin determination at 10 min intervals. The glucose infusion rate during steady state was used to characterize insulin sensitivity.

From the examinations the following results were obtained:

1. The relaxation response to cumulative increases in acetylcholine concentration (1 nm–10 µM) was not modified by 1 µM of the compounds of the invention in the vessel of normal rabbits.
2. In experimental hypercholesterolaemia, vasorelaxation by acetylcholine was significantly smaller in the presence of the compounds of the invention.
3. Field stimulation induced an increase in tension in carotid artery rings incubated in Krebs solution. In NANC solution, however, a relaxation response was observed in response to the stimulation protocol applied. Neither response was influenced by the compounds of the invention.
4. Removal of the endothelium significantly increased contraction produced by field stimulation and decreased NANC relaxation. The compounds of the invention alleviated contractions produced by field stimulation and augmented NANC relaxation in endothelium-free vessel rings.
5. Field stimulation-induced contractions were augmanted, whereas the NANC relaxation responses were attenuated in vessel rings from hypercholesterolaemic animals compared to those seen in preparations from normal rabbits. The compounds of the invention significantly decreased electrical stimulation-induced contractions and amplified the NANC relaxation response in rings from hypercholesterolaemic rabbits irrespective of the presence of endothelium.
6. Baseline cyclic GMP concentration was significantly decreased in rings from hypercholesteroaemic rabbits compared to that in normal rings. This decrease was almost normalized by incubation with 1 µM of the compounds of the invention. The compounds tested were, however, without effect on resting cyclic GMP content in normal rings. Field stimulation produced an increase in cyclic GMP concentration in preparations from normal animals. In rings from hypercholesterolaemic rabbits, the stimulation protocol applied failed to elicit any increase in cyclic GMP. The compounds of the invention were without effect on the field stimulation-induced increase in tissue cyclic GMP content in normal rings but a substantial cyclic GMP increase was seen in preparations from hypercholesterolaemic rabbits.
7. Exposure to cholesterol-enriched diet resulted in a marked decrease in insulin sensitivity in conscious rabbits. Treatment with the compounds of the invention over 4 days almost restored insulin sensitivity in hypercholesterolaemic animals. However, the compounds of the invention were without effect on insulin sensitivity in normal animals.
8. 7-nitroindazole, an inhibitor of neural nitric oxide synthase produced insulin resistance in normal animals by itself. The compounds of the invention failed to modify this insulin resistant state. Moreover, 7-nitroindazole blocked the insulin resistance ameliorating effect of the compounds of the invention in experimental hypercholesterolaemia.

Conclusions:.

The results presented show that the compounds of the invention increase the hypoglycaemic effect of insulin in insulin resistant state associated with experimental hypercholesterolaemia in conscious rabbits. The results also provide evidence that this insulin sensitizing effect is strongly related to nitrergic pathways, the influence of which has recently been suggested to play a major role in regulating insulin sensitivity [Shankar, R. R. et al., Diabetes, 49, 684–687 (2000)]. The hepatic neurohormonal regulation of peripheral insulin sensitivity can be described as follows [Lautt, W. W., Can. J. Physiol., 77, 553–562 (1999)]:

There is a postprandial increase of blood level of insulin.

In response to this insulin level increase, hepatic parasympathetic reflex is activated.

This reflex causes the release of acetylcholine which activates muscarinergic receptors.

The muscarinergic excitation leads to the release of nitrogen oxide (NO).

Only in fed state, nitrogen oxide causes the release of a hepatic insulin sensitizing factor (HISS) which possesses insulin synergent or insulin-like effect.

HISS increases the glucose uptake of skeletal muscles.

This HISS mechanism is sensitive to the blockade of nitrogen oxide synthesis and can be activated by exogenous NO-donor. It is very likely that HISS mechanism is closely related to the function of hepatic sensory fibers. The postprandial increase of plasma insulin level activates the nitrergic subpopulation of hepatic sensory nerve fibers which evoke the release of sensory neurotransmitters from the neighboring fibers. These sensory neurotransmitters, via their hormon-like character, reach the blood stream and elevate the insulin sensitivity of the tissues.

In a very recent work Steppan et al. shed light on the missing link between obesity and insulin resistance [Steppan, C. M. et al., Nature, 409, 307–312 (2001)]. In brief, a hormone termed resistin is produced by adipocytes. Resistin was shown to decrease the sensitivity of target tissues (fat and skeletal muscle) to the hypoglycaemic effect of insulin. Therefore, pharmacological inhibition of resistin secretion is a possible new mechanism of action for pharmacological exploitation in the treatment of non-insulin-dependant diabetes mellitus and the insulin resistance syndrome. Among the currently known drugs, members of the thiazolidinedione family can inhibit insulin secretion through the peroxisome proliferator activator gamma nuclear receptor in the adipocytes.

The compounds of the formula I have an effect on the insulin sensitivity, and they are able to alleviate insulin resistance through nitrergic mechanism and sensory neurotransmitters. The normalization of insulin sensitivity have causal role in diseases of high morbidity and mortality such as type II diabetes, hypertension, coronary heart disease, obesity and some endocrine diseases.

Use of the Compounds of the Invention for the Prevention of Toxic Effects

1) Effect of the Compounds on the Lethality Induced by Endotoxin in Mice

The septic shock is one of the most frequent cause of death in intensive wards. Infections caused by Gram-negative bacteria lead to hypotension, to insufficient function of several organs, and, at last, to the collapse of the organism. Through the injection of lipopolysaccharide (LPS)—a component of the bacterium membrane—into experimental animals, a shock-like state and, lastly, death are produced. LPS activates the NF-κB/Rel transcription family that regulates the production of several transmitters taking part in the pathomechanism of shock (such as TNF-α, interleukines, NO syntase) [Oliver, F. J. et al.: Resistance to endotoxic shock as a consequence of defective NF-κB activation in poly(ADP ribose) polymerase-1 deficient mice, EMBO J., 18 (16), 4446–4454 (1999)]. The PARP-1 gene is connected to NF-κB functionally, thus, in lack of PARP, the transcriptions depending on NF-κB do not proceed either, consequently, also the release of inflammation mediators becomes underregulated in endotoxin shock. The aim of the test is to determine whether the lethality caused by endotoxin could be prevented through the inhibition of PARP-1 by the compounds of the formula I.

For the experiments, C57BL/6 mice (Charles River Breeding Ltd.) were employed. In the test, the dose and type of the LPS used were identical with those described in the article of Oliver, F. J. mentioned above: lipopolysaccharide from *Escherichia coli* 0111:B4 (Sigma). In the experiments, also 3-amino-benzamide (Sigma) was used. The 24 hours survival was followed at least twice. The compounds of the formula I were administered to the animals, perorally, 1 and 6 hours after the treatment with LPS.

It was found that the lethality produced by endotoxin was significantly reduced by the compounds of the formula I tested.

2) Effect of the Compounds on the Hepatotoxicity Induced by Acetaminophene (Paracetamol)

It is known that various non-steroid antirheumatics [Peters, M. et al., Clin. Inves., 71, 875–881 (1993)] and analgetics, respectively, have significant hepatotoxicity [Kröger, H. et al., Gen. Pharmac., 27, 167–170 (1996)]. Liver and kidney insufficiencies are induced by a large dose of paracetamol [Meredeth, T. J. et al., Arch. Inter. Med., 141, 397–400 (1981)]. Recently it became obvious that the poly (ADP ribose)-polymerase inhibitors eliminate the liver damage induced by paracetamol [Kröger, H. et al., Gen. Pharmac., 27, 167–170 (1996)]. It is known from the literature that paracetamol is the inducer of cytochrom P-450. The effect of paracetamol on the cytochrom P-450 system produces reactive quinone imines that bind to the sulfhydryl group of proteins, thus, resulting a fast depletion of the intracellular glutathion [Jollow, D. J. et al., Pharmacol., 12, 251–271 (1974)]. The inactivated proteins lead to the destroy of liver cells and liver necrosis, respectively. The intracellular glutathion is one of the most important antioxidant and the strongest eliminator of reactive oxygen species, respectively. The weakening of the antioxidant protective system that depends on glutathion leads to an increase of the intracellular level of free oxygen radicals [Miesel, R. et al., Inflamatin, 17, 283–294 (1993)]. The free oxygen radicals are strong PARP inducers influencing the post-translation of proteins. Due to the increased PARP activation, the NAD stores of the cells are depleted and apoptosis may be started [Hoschino, J. et al., J. Steroid Mol. Biol., 44, 113–119 (1993)]. Therefore, the nicotinic amide—a selective inhibitor of the PARP enzyme—suppresses the release of the GOT and GPT enzymes in the liver as shown in mice in case of hepatitis induced with paracetamol [Kröger, H. and Ehrlich, W. in: L-Tryptophan: Current Prospects in Medicine and Drug Safety, Edited by Kochen, W. and Steinhart, H., Verl. Belin, 1994].

It was examined whether the liver damage induced with paracetamol can be prevented by the novel compounds of the formula I. The symptom of liver damage was characterized by an increase of the GOT and GTP enzyme levels induced with paracetamol. The experiments were carried out on male NMRI mice of 30–40 g body weight. The animals were pretreated with the compounds of the formula I, perorally, for 7 days. On day 8, the mice were subjected to starvation for 12 hours, then a 500 mg/kg p.o. dose of paracetamol and a given dose of a compound of the formula I were administered. After 16 hours, the animals were bled to death and the activity of the GOT and GPT enzymes was measured in the serum. The results were analyzed by the non-parametric test of Mann and Whitney. As to the results, the average and the standard deviation are given wherein $p<0.05$ was considered as significant.

It was found that a single peroral administration of paracetamol enhanced the activity of GOT and GPT in the serum of male NMRI mice relative to the control animals treated with physiological salt solution. However, the compounds of the formula I, after a peroral pretreatment lasting for 7 days, reduced the activity of the GOT and GPT enzymes very significantly. For example, very favourable hepatoprotective effect has been observed in case of the compound of Example 12 administered in a dose of 50 mg/kg.

3) Effect of the Compounds on the Toxicity of Paraquat

Paraquat [1,1'-dimethyl-4,4'-bipyridinium], a compound used earlier as a pesticide, exerts a toxic action through the formation of superoxide radical. Oxidoreductase enzymes that use NADH and NAD(P)H as electron donors take part in the formation of the superoxide radical. [NAD(P)H is β-nicotinamide adenine dinucleotide phosphate, reduced form]. In the transmission of the cell response to the oxidative stress induced by paraquat, the protein p66 plays an important role [Migligaccio, E. et al., Nature, 402, 309–313]. The mechanisms contributing to the inactivation of superoxide (such as the increase of the superoxide dismutase level) reduce the toxicity of paraquat effectively. The superoxide radical has an important role in the patomechanism of several diseases (such as ischemia reoxygenation, infarction, inflammatory diseases). A simple model of the superoxide load experienced in these diseases is obtained by the administration of paraquat.

Effect on the Toxicity of Paraquat, In Vitro

Hepa-1 hepatoma cells were grown in RPMI-1640 medium supplemented with 10% of calf serum, while PC-12 rat pheochromocitoma cells were grown in RPMI-1640 medium supplemented with 10% of calf serum and 5% of horse serum at 37° C. in an air containing 5% of carbon dioxide. Using 100 μl of culture medium, $5 \times 10^3$ cells were plated in the wells of a 96 well Costar culture plate. A part of the cultures did not obtain any treatment and was used as the control. The cells were treated partly with increasing concentrations of paraquat, partly with the same concentration of paraquat and 3, 10 and 30 μg/ml concentration of the test compounds. The cells were grown for further 3 days, then stained with SRB. Higher paraquat concentrations resulted in the death of the cells, while lower concentrations of paraquat inhibited the cell growth partially. The effect of the compound to be tested was determined on the basis of lowering the toxicity of paraquat.

Effect on the Toxicity of Paraquat, In Vivo

Paraquat has significant toxicity in mice. A dose of 70 mg/kg administered intraperitoneally results in the death of the animals within 2 days. The mechanisms that moderate the superoxide formation, the neutralization and the effects of the oxidative stress are able to lower the toxicity of paraquat also in vivo.

CFLP mice having a body weight of 20–22 g were divided into groups consisting of 10 animals and treated, intraperitoneally, with 50 and 70 mg/kg of paraquat, respectively. A part of the groups were also treated with the test compound 6 hours before and after the administration of paraquat. In case of the test compounds, a po. dose of 100 mg/kg was employed. The efficacy of the test compounds was determined on basis of the increase of the survival of the mice.

It was found that the compounds of the formula I reduced the toxicity of paraquat significantly.

Effect of the Compounds of the Formula I on Neurodegenerative Diseases

As it has been mentioned earlier, owing to the DNA damage by ROS, the PARP enzyme is being activated which is followed by the cell loosing NAD, thus, leading to cell death. An extreme rate of PARP activation cannot solely be observed during neuron death caused by ischemia like brain ischemia, but has a proven role in other neurodegenerative diseases such as Alzheimer's disease, Parkinson's disease and amyotrophic lateral sclerosis [Love et al., Neuropathol. Appl. Neurobiol., 25, 98–108 (1999); Eliasson et al., Nat. Med., 10, 1089–1095 (1997)].

Effect on Experimental Amyotrophic Lateral Sclerosis

Amyotrophic lateral sclerosis (ALS) is a fatal progressive neurodegenerative disease. It is the most common adult onset motor neuron disorder in developed countries. ALS involves motor neuron degeneration in the cortex, brain stem and spinal cord that causes skeletal muscle atrophy, paralysis and death [Rowland, L. P. in Neurodegenerative diseases, pp. 507–521 (1994)]. In a part of the ALS cases, the disease is familial. The familial cases are partly caused by the missense mutation of Cu/Zn superoxide dismutase-1 (SOD-1) gene [Deng, R. H. et al., Science, 261, 1047 (1993)]. SOD-1, a cytosolic enzyme abundant in nerve tissue, plays an important role in protection against oxygen radical induced cellular damage. The mutated enzyme maintains near normal level of enzyme activity. In vitro studies indicated that SOD-1 mutations result in a gain of function and enhance free radical generation.

Transgenic mouse having mutated SOD-1 gene develops symptoms similar to those of ALS. Several human mutated SOD-1 genes (G93A, V148G) have already been overexpressed in transgenic mouse and the generated disease models were applied for anti-ALS drug screening [Gurney, M. E., J. Neurol. Sci., 152 Suppl. 1, 67–73 (1997)].

Test on Familial ALS Model

Transgenic mice overexpressing the mutated human SOD-1 gene (G93A) were used in the study. Animals were purchased from the Jackson Laboratory, USA. Treatment with the compounds of the formula I started before the appearance of symptoms of the disease at the age of 4 weeks. The test compounds were applied once a day, perorally, at 3 dose levels till the termination of the experiment. The progression of the disease was monitored by weekly examination of motor performance (extension reflex, loaded grid, rotarod test), by the survival time and, at the termination of the experiment (after 120 days), by histological and biochemical examination of motor neuron areas.

It was found that the compounds of the formula I resulted in a moderate delay of the appearance of the reflex, coordination and muscle strength deficit in transgenic ALS animals. The effect showed dose dependence. There was also a delay in the appearance of the paralysis and the end stage disease. Results of histological examination confirmed the observed clinical effect of the treatment. Degeneration and loss of motoneurons and substancia nigra neurons were less extended in the treated than in the control group. On basis of the results it can be expected that the compounds of the formula I have a favourable therapeutic effect in ALS diseases.

Test on Autoimmune ALS Model

In case of sporadic ALS diseases, no mutation can be found in the SOD-1 gene. This fact suggests that other causes lead to the same progress of disease. In most patients suffering from sporadic ALS, the antibody against calcium channels can be detected. This observation confirms the concept that an autoimmune process against motoneurons and calcium channels plays a primary causal role in the formation of the sporadic ALS cases. In experimental animals, Engelhardt and coworkers induced a disease showing the specific alterations of ALS by immunization with motoneuron, then using merely immune serum [Engelhardt, J. et al., Synapse, 20, 185–199 (1995)]. This model was used for testing the efficacy of the compound of the formula I in sporadic ALS diseases.

Hartley guinea pigs were immunized with homogenized bovine anterior horn spinal cord. For the immunization, the moto-neurons were suspended in complete Freund's adjuvant (CFA). The treatment was performed by 10 subcutaneous or intracutaneous injections, injecting 0.1 ml of suspension each time. After a month, the injections were repeated, however, incomplete Freund's adjuvant was used for the preparation of the suspension. Two weeks after the second immunization, within 1–3 days, severe weakness developed in the animals, especially in the lower limbs. The gain of body weight stopped, the motility lowered. During further two weeks, the state of the animals did not change. Then the animals were bled to death. The blood collected was centrifuged to obtain the serum that was used to induce ALS in mice.

The tests were performed on groups consisting of 5 male albino mice (CFLP, 25–30 g body weight). 1 ml of the above serum was injected intraperitoneally into each animal to damage the motoneuron. One of the animal group was treated only with the serum, while other animal groups were treated, in addition to the serum, also with a test compound of the formula I in a dose of 100 mg/kg, intraperitoneally. Further animal groups were treated only with the test compound of the formula I without the injection of serum.

The motility of the animals treated only with the serum became slow, the lower limbs could be used only with difficulties, then they became paralyzed. In case of the animals treated with both the serum and a test compound of the formula I, no symptom of motor deficit could be detected. The same was experienced in case of the animals treated only with the test compounds of the formula I. All this suggests that the compounds of the formula I prevent the development of motor disturbances that can be induced by immunization.

Effect on the Experimental Model of Parkinson's Disease

Parkinson's disease (PD) is a common disabling idiopathic neurodegenerative disorder characterized by tremor, bradykinesia, rigidity and balance difficulties. These motor abnormalities are caused by the depletion of brain dopamine that results from the loss of dopaminerg neurons in the substantia nigra pars compacta. The analysis of the action of 1-methyl-4-phenyl-1,2,3,6-tetrahydropyridine (MPTP) having selective neurotoxicity shed light to the possible patomechanism of the Parkinson's disease. MPTP induces parkinsonian motor signs in both human and animals [Dexter, A. et al., Ann. Neurol., 35, 38–44 (1994)]. MPTP treatment results in a loss of dopaminergic neurons in the substantia nigra pars compacta, as well. Lewy body-like eosinophilic inclusions appear in the damaged neurons and the activity of mitochondrial complex I is also diminished in these cells. These alterations are characteristic for oxidative stress [Shapira, A., Adv. Neurol., 69, 161–165 (1996)]. The biologically active metabolite of MPTP is MPP [1-methyl-4-phenylpyridinium]. MPP inhibits directly complex I in mitochondria leading to increased generation of superoxide anion. Data indicate that oxidative stress plays a central role in the pathogenesis of the natural form and of the MPTP induced form of Parkinson's disease. The PARP enzyme is activated by the oxidative stress, and the enzyme seems to play an active role in the pathomechanism of the Parkinson's disease. PARP knockout mice show a greatly reduced sensitivity against the Parkinsons disease inducing effect of MPTP [Mandir, A. et al., Proc. Natl. Acad. Sci. USA, 96, 5774–5779 (1999)]. These findings suggest that PARP inhibition may result in therapeutic effect in Parkinson's disease. C57BI mice employed in the tests were purchased from Charles River Hungary. The mice weighing 20 g were treated four times with 20 mg/kg of MPTP each time administered at 2 hours intervals, intraperitoneally. The test compounds were administered perorally at 30 min before the injections of MPTP. The control animals received vehicle treatments at the same rate. Seven days after the MPTP injection, mice were sacrificed and brains were quickly removed. Striata were dissected on ice-cold Petri dish. Excised tissues were immediately frozen and kept at −80° C. until analysis. Tissue samples were sonicated in 50 volumes of 0.1 M perchloric acid to achieve homogenization. After centrifugation (14000×g, 10 min, 4° C.), 20 μl of supernatant were injected onto a reverse phase catecholamine column (ESA, Bedford) and dopamine content was evaluated.

2 hours after the last MPTP treatment, ventrolateral midbrain and striata were excised and homogenized in a sucrose/DTT buffer, then centrifuged (14000×g, 5 min). The pellet was resuspended in the buffer. After determination of the protein concentration, equal amount of protein was loaded on a SDS/PAGE gel. The protein was transferred from the gel to a nitrocellulose membrane and immunostained for poly(ADP ribose) polymer. Specific binding was visualized by chemiluminescence.

In the examinations it was found that MPTP treatment caused a drastic decrease (by 80%) in striatal dopamine content. The test compounds of the formula I partially (by 20–40%) inhibited the dopamine loss induced by MPTP. The MPTP treatment resulted in the appearance of poly(ADP-ribose)polymer adducts in the striatal area. Concomitant treatment with the test compounds produced an inhibition of this process (by 20–70%). Thus, it can be expected that the compounds of the formula I may have therapeutic activity in Parkinson's disease.

Examination of the Cytoprotective Effect

Some drugs used permanently or frequently can cause neuronal damage as adverse effect. From a large series of such drugs causing this adverse effect (chloramphenicol, dapsone, disulfiram, dichloroacetate, ethionamide, glutethimide, sodium aurothiomalate, hydralazine, isoniazid, metronidazole, nitrofurantoin, nitrous oxide, cisplatin, pyridoxine, vincristine) the best characterized and most frequently discussed are the neuropathies induced by isoniazid, pyridoxine, vincristine or cisplatin. Chloramphenicol is the drug which can elicit such a neuropathy, but this adverse effect may disappear after cessation of treatment. However, in almost all clinical cases, the premature stop of chemotherapy may prevent the success of the treatment and may cause the revival of the disease. Especially high is the danger of therapeutical treatment changes due to side-effects in cases of anticancer chemotherapy. This fact gives great importance to the so-called chemoprotective or cytoprotective agents which are able to diminish the injurious adverse effect of the important life-preserving drugs without causing any decrease of the therapeutic effectivity.

In cancer patients treated with cisplatin, the major side-effect is the injury of peripheral nerves (peripheral neuropathy). The onset of this side-effect may hinder the performing of the cisplatin treatment, may endanger the success of the treatment, and impairs the life quality of the patients. The presence and grade of neuronal damage can be determined by the measurement of the nerve conduction velocity in both clinical and experimental studies. Neurotoxic effect of cisplatin [cisdiammine dichloroplatinum] involves, primarily, the large myelinated peripheral nerves and manifests in sensory neuronal damage (sensory neuropathy). Recently, some reports mention autonomic neuropathy and, occasionally, also motor neuropathy following treatment with cisplatin. Through damaging directly the dorsal root ganglia and large sensory nerves, cisplatin can often cause the functional disorder of the sensory nerves. In rats, the chronic cisplatin treatment elicits sensory neuropathy which is reflected in the slowing of the sensory nerve conduction velocity of the mixed type ischiatic nerve.

On the basis of the biochemical mode of action mentioned above, mainly by preventing the injuries caused by free radicals, it was believed that the compounds of the formula I may have cytoprotective potential and may prevent the organotoxic adverse effects of antitumor drugs. Therefore, in rat experiments cisplatin was given in form of a subacute treatment for 10 weeks in doses of 1 and 2 mg/kg i.p., and the development of peripherial neuropathy was observed. Furthermore, it was examined how the different doses of the test compounds influence the injury of the nerve function (nerve conduction velocity).

To detect the sensory and motor neural injury induced by cisplatin, the nerve conduction velocity was measured at the tail of the rats according to the modified method of Miyoshi. The modification consisted of measuring the nerve conduction velocity at room temperature instead of 37° C. Sensory and motor nerve conduction velocities were determined before the cisplatin treatment (control) and in the $5^{th}$ and $10^{th}$ treatment week. During the measurement, animals were superficially anaesthetized by ether and two pin electrode pairs were placed to the tail nerve in a distance of 50 mm from each other. Using supramaximal stimulus strength, afferent (motor) and afferent (sensory) nervous action potentials were recorded. The nerve conduction velocity was determined off-line by averaging 10 action potencials using the formula $NCV = v/l$ [m/sec], wherein v=distance between trigger and registratory electrode pairs in mm,
l=latency time of the onset of action potential in msec,
NCV=nerve conduction velocity in m/sec.

In the tests it was found that 10 weeks' treatment with 1 and 2 mg/kg of cisplatin i.p. reduced the body weight of the treated animals significantly relative to that of the control animals. This reduction of body weight was experienced also in case of the animals treated with the compounds of the formula I. There was no difference in the general behaviour between treated and untreated animals or animals treated with cisplatin and a test compound. There was no difference in NCV of sensory and motor nerves in the control group in the three measuring times. In the animals treated with cisplatin, NCV decreased unanimously and remarkably in the fifth and also in the tenth week due to the treatment with 1 mg/kg of cisplatin. After the treatment with 2 mg/kg of cisplatin, a stronger reduction of NCV was experienced. Neuropathy developed also in the motor nerves.

In the course of cisplatin treatment for 10 weeks, the motor NCV decreased significantly in both 1 and 2 mg/kg of cisplatin dose groups. The decrease was dose dependant. In the groups treated with both 1 mg/kg of cisplatin and a compound of the formula I, the decrease of sensory nerve conduction velocity was significantly less than in the group treated only with 1 mg/kg of cisplatin, thus, this neuronal function improved following combined treatment. The degree of improvement was the higher the stronger was the degree of injury. In the group treated both with 2 mg/kg of cisplatin and a compound of the formula I in various doses, in the fifth week the decrease of sensory nerve conduction velocity did not differ from that of the group treated only with 2 mg/kg of cisplatin. In the tenth week, however, the group of animals treated only with 2 mg/kg of cisplatin decreased significantly further, while in case of the animals treated with both cisplatin and a compound of the formula I, the decrease was dose-dependant compared with the animals treated only with 2 mg/kg of cisplatin. The decrease of the afferent nerve conduction velocity was lower at the end of the tenth week, especially in the groups treated also with the compounds of the invention.

Summing up, it can be stated that the injury of sensory and motor nerve conduction velocities caused by cisplatin treatment was decreased by the simultaneous treatment with the compounds of the formula I, and the progress of the injury from the fifth to the tenth week was prevented. This protective effect was dosis dependant in some groups. Thus, the neuro-protective effect of the compounds of the formula I can be demonstrated in both sensory and motor nerve functions.

Biological Effect of Carnitine-Palmitoyl Transferase (CPTI)

The CPTI is a key enzyme in the regulation of fatty acid metabolism. There are two possibilities for the coenzyme A esters (CoA) of free fatty acids (FFA):
 1) triglyceride synthesis through reaction with glycerol or
 2) oxidation, the first step of which is the formation of acylcarnitine by means of CPTI enzyme [see McGarry, J. D. et al., Diabetes, 5, 271–284 (1989); McGarry, J. D. and Foster, D., Ann. Rev. Biochem., 49, 395–420 (1980)]. The CPTI enzyme is localized at the outer part of the inner mitochondrial membrane (or at the outer membrane) and catalyzes the following reaction:

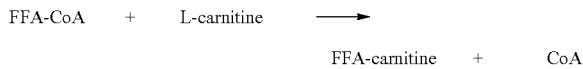

The inhibition of fatty acid oxidation results in the increase of glucose breakdown and oxidation. This process is extremely significant and advantageous, especially in myocardial ischemia and diabetes; both of these pathological states have high morbidity and mortality. In myocardial ischemia and in the subsequent reoxygenation, the enhanced fatty acid oxidation is detrimental because of the extra oxygen demand and the membrane damaging effect of the acylcarnitines formed [Busselen, P. et al., J. Mol. Cell. Cardiol., 20, 905–916 (1988); Ford, D. A. et al., Biochemistry, 35, 7903–7909 (1996); Reeves, K. A. et al., J. Pharm. Pharmacol., 48, 245–248 (1995)]. On basis of several experimental data, nowadays it is an accepted fact that the activation of glucose metabolism and the simultaneous inhibition of fatty acid oxidation have favourable effect from the point of view of both restoration of the mechanical function of the myocardium and the parameters of metabolism (enzyme release, lipid peroxidation) [Lopaschuk, G. D. et al., Circ. Res., 66, 546–553 (1990); Kennedy, J. A., et al., Biochem. Pharmacol., 52, 273–280 (1996)]. This substrate selection of the myocardium i.e. the choice between glucose and fatty acid can be achieved also by CPTI inhibitors, thus, the glucose utilization is increased and the energetics of the myocardium is improved [Lopaschuk, G. D. et al., Circ. Res., 63, 1036–1043 (1988); Carregal, M. et al., Arch. Phys. Biochem., 103, 45–49 (1995); Lopaschuk, G. D. et al., 65, 378–387 (1989); Pauly, D. F. et al., Circ. Res., 68, 1085–1094 (1991)].

Our studies show that the enzyme that catalyzes the rate-limiting reaction of the fatty acid oxidation can be inhibited by the compounds of the formula I in sub-millimolar concentration range. The studies also indicate that the test compounds influence the substrate selection of heart and other tissues and, through the change of substrate selection, also the postischemic damages of the tissues.

The Biological Role of Oxygen Sensitive Genes Regulated Primarily by bHLH Transcription Factors Protection against the harmful effects of hypoxia requires a series of organized defensive reactions both at the level of the individual cells and at the level of the whole organism. In regulation of the expression of hypoxia induced genes, the HIF-1/ARNT transcription complex plays a central but not exclusive role. Oxygen sensitive, coordinately regulated genes include erythropoietin which stimulates the production of red blood cells [Wang, G. L. et al., PNAS, 92, 5510 (1995)], VEGF (vascular endothelial growth factor) which stimulates angiogenesis [Goldberg, M. A. and Schneider, T. J., J. Biol. Chem.,269, 4355 (1994)], glycolitic enzymes likes GAPDH, LDH (lactate dehydrogenase) [Rolfs, A. et al., J. Biol. Chem., 272, 20055 (1997)], as well as the glucose transporter Glut-1.

The compounds of the formula I are presumably binding to the ARNT and/or HIF-1 transcription factors, thus, they can influence the activation of genes that take part in the alarm (hypoxia sensitive) states. It is believed that, through this signal transduction pathway, the compounds of the invention express the heat shock proteins playing an important role in alarm situations.

Synthesis of heat shock proteins (HSP) is induced by various stresses that effect the cells. Heat shock proteins help the survival of cells in dangerous situations and contribute to the reparation of any damages [Cardiovascular Res., 578 (1993); Neurosci. Lett., 163, 135–137 (1993)].

Agents which can facilitate the alarm reaction in the adaptation to hypoxia, to reoxygenation and restore the exhausted adaptation reaction are potentially able to diminish tissue damage caused by hypoxia (hypoxia-reoxygenation) in diseases like infarction, arteriosclerosis and diabetes.

Determination of HSP-70

The activity of HSP-70 was studied by reporter gene assay forming a DNA hybrid. A gene of a protein that can be detected by a well-measurable enzyme activity was fused to the promoter sequence of HSP-70 encoding the heat shock protein. Biotechnological processes were used. Luciferase enzyme was used as the reporter gene the activity of which can be well determined by luminescence measurement. If the promoter of the gene of the luciferase enzyme is substituted by the promoter of the HSP-70 gene, then the change in the activity of the luciferase enzyme i.e. the change of the frequency of the transcription from the gene correlates with the frequency of the transcription of the HSP-70 gene that proceeds in the given circumstances. In this way, if a substance or process influences the expression of the HSP-70 gene, the effect can be studied through the measurement of the luciferase enzyme activity. The effect of the test compounds on the HSP-70 expression was studied in such an experimental system.

A double-stranded DNA circular molecule i.e. a plasmid containing the HSP-70 reporter gene was constructed to perform the measurements. An almost 600 bp long sequence of the mouse HSP-70 gene promoter (5' direction from the start site of the gene) was fused to the coding sequence of the luciferase gene originated from Photymus pyralis. The applied promoter sequence contained several protein binding sites facilitating the expression of the HSP-70 gene. The HSP promoter-luciferase heterologous gene construct was built in a pBR based plasmid vector that can be selected for neomycin. This HSP-70-luciferase plasmid was transfected into mouse fibroblast L929 cells. The assay was performed as follows: L929 cells that contain the HSP-70-luc plasmid are grown in DMEM (Dulbecco's Modified Eagle's Medium) supplemented with 5% FCS (Fetal Calf Serum). $10^4$ cells are plated in the wells of a 24-well Costar cell culture plate in 1 ml of culture medium. Test substances are dissolved in PBS (Phosphate Buffered Saline) in $10^{-2}$ M concentration. After attachment of the cells (3–4 hours after plating), 10 μl of the solution are given to the cultures and cells are incubated for 30 min at 37° C. in a $CO_2$ thermostat. Culture medium is then changed for fresh one (without test substance), and cells are allowed to regenerate for 1 hour at 37° C., then once washed with PBS. After removal of PBS, 40 μl of 1× lysis buffer are added to the cells, and the samples are kept on ice for 30 minutes. Then, the cells are transferred into Eppendorf vials and centrifuged at 14000 rpm for 20 min at 4° C. 5 μl of the supernatant is added to 25 μl of luciferase assay buffer and the luminescence of the samples is measured for 25 s in a luminometer.

Composition of the luciferase assay buffer:
20.00 mM of tricin [N-/2-hydroxy-1,1-bis(hydroxymethyl)ethyl/glycine], pH 7.8,
1.07 mM of $(MgCO_3)_4$ $Mg(OH)_2.5H_2O$,
2.67 mM of $MgSO_4$,
0.10 mM of EDTA [ethylenediaminotetraacetic acid],
3.33 mM of DTT,
270 μM of coenzyme A lithium salt,
470 μM of luciferine,
530 μM of ATP [adenosine triphosphate].

Composition of 5× lysis buffer:
125 mM of tris-$H_3PO_4$ pH 7.8,
10 mM of CDTA [trans-1,2-diaminocyclohexane-N,N,N', N'-tetraacetic acid],
10 mM of DTT,
50% of glycerol,
5% of Triton X-100.

Study of Hypoxia Sensitive Genes

The effect of the compounds of the formula I was studied on xenobiotic and hypoxia (1% of oxygen) induced gene expression in Hepa and HepG2 cell cultures at mRNA and protein levels. It was observed that the compounds of the formula I resulted in a 10-fold increase in the methylcholanthrene induced HSP-70 expression in Hepa cells. Furthermore, the compounds of the invention increase the expression of hypoxia sensitive genes like VEGF, GAPDH and LDH in response to hypoxia treatment in Hepa and HepG2 cells.

The compounds of the formula I increase the expression of several hypoxia sensitive genes in case of hypoxia. This indicates that the test compounds influence the common pathway in the regulation of oxygen sensitive genes. The compounds of the formula I facilitating the adaptation to stress caused by hypoxia and hypoxia-reoxygenation are suitable for protection against the harmful effect of hypoxia and hypoxia-reoxygenation. It is expectable that the compounds provide therapeutic benefit in conditions where tissue damage is caused by circulatory disturbance, constriction and spasm of arteries, arteriosclerosis, infarction, embolism, thrombosis, low blood pressure, shock, burning, freezing. The compounds of the invention may be effective in secondary hypoxic conditions associated with degenerative and metabolic diseases (Alzheimer's disease, diabetes) as well.

Effect on the LDH Enzyme Level in Hypoxia Exposed HepG2 Cells

HepG2 cells were cultured in DMEM medium supplemented with 10% of FCS in an air containing 5% of $CO_2$ at 37° C. $10^5$ cells Were plated in the wells of Costar 24-well culture plates in 1 ml of medium. On the following day, cells were treated with the test compounds in a concentration of 30 μg/ml, then the cells were exposed to hypoxia treatment (1% of $O_2$, 5% of $CO_2$ in nitrogen gas) for 24 hours. A part of the control cultures were treated with water used as the solvent, another part of them was not exposed to hypoxia. At the end of the hypoxic treatment, medium was removed and cells were washed twice with cold PBS. Cell lysates were prepared in 0.05% Triton X-100 containing phosphate buffer (0.05 M). After centrifugation (2 min, 20000×g), the LDH activity of the supernatant was determined on the basis of NADH consumption in the presence of sodium pyruvate substrate.

The applied hypoxic treatment induced a 3-fold increase in the LDH content of the cells. In addition to the treatment of hypoxia, the compounds of the formula I enhanced the LDH level of the cells in an additive manner.

Antiviral Effect

The retroviral genome consists of a single stranded RNA molecule which replicates through a double stranded DNA intermediate. Insertion of the double stranded DNA into the host genome is a critical event in the life cycle of the virus. The mechanism of insertion is similar to the mechanism of transposition.

The enzyme reverse transcriptase makes the DNA copy of the viral RNA. The double stranded DNA is synthesized in the cytoplasm of the infected cell. Then, the linear DNA is transported into the nucleus and one or more copies are integrated into the genome of the host cell. The integration is mediated by the integrase enzyme. When the proviral DNA is integrated, it uses the enzymes of the host cells to produce viral RNA which serve as mRNA and as the genome after packaging into the virions.

In the process of virus replication, the untroubled function of reverse transcriptase is essential. Therefore, the inhibition of reverse transcriptase provides an efficient way to inhibit the replication of retroviruses. A part of the presently available anti-HIV drugs acts through the inhibition of the reverse transcriptase. Currently, the most efficient anti-HIV treatments are based on combinations of various anti-HIV drugs. One or two components of these combinations are reverse transcriptase inhibitors. There are two major types of reverse transcriptase inhibitors. One consists of the nucleoside analogues, the well known representative of this group is the azidothymidine i.e. AZT. These compounds inhibit the enzyme activity by binding to the nucleotide binding site. The non-nucleoside analogues represent the other type of reverse transcriptase inhibitors. These compounds are binding also to the enzyme, but not to the nucleotide binding site. The binding is specific, relatively stable and results in the deformation of the enzyme active site causing significant loss of enzyme activity.

The reverse transcriptase inhibitory activity of the compounds of the invention was studied as follows. These compounds may be classified as non-nucleoside analogue reverse transcriptase inhibitors. Tests were performed on Moloney murine leukemia virus reverse transcriptase that is considered as a good model of the HIV reverse transcriptase enzyme. The experimental assembly was the following:

The assay measures the incorporation of (3H)dTTP into cDNA using poly(dA) template and oligo(dT)12-18 primer. The reaction was carried out in 20 μl volume.

Composition of the reaction mixture:
2 μl of 10× buffer,
20 μl of template primer,
5 μM of dTTP,
2 μCi of (3H)dTTP,
test compound: dissolved in 1× buffer.
The reaction was started by the addition of 5U of reverse transcriptase.
Composition of the 10× reverse transcriptase buffer:
500 mM of tris-HCl pH 8.3,
80 mM of $MgCl_2$,
300 mM of KCl,
100 mM of DTT.

The reaction mixture was incubated for 40 min at 37° C. Then, 15 μl of reaction mixture was loaded on Whatman DE81 filter discs which were washed, sequentially, with 5% disodium hydrogen phosphate buffer, water and 96% (v/v) ethanol. After drying, the filter discs were placed into 5 ml of scintillation cocktail (OptiPhase HiSafe 3, Wallac), and the radioactivity was measured in a Packard Tri-Carb 2200 CE scintillation counter.

Two compounds with known inhibitory activity were used in the experiments as positive control: AZT is a nucleoside analogue, while the compound Nevirapin is a non-nucleoside type inhibitor. Nevirapin is binding to the so called benzodiazepine binding site of the enzyme.

The experimental results provide the following conclusions: The compounds of the invention inhibit the Moloney murine leukemia virus reverse transcriptase. The test compounds were employed in concentrations of 0.2–2.0 μg/ml. On the basis of the dose dependent reverse transcriptase inhibitory activity, it can be stated that the inhibiting effect of the novel compounds is higher than that of Nevirapin, but lower than the effect of the nucleoside analogue AZT. Since the used enzyme is considered as a true model of the HIV reverse transcriptase, the observed results can be considered as anti-HIV effects.

Recent data show that PARP is necessary for the integration of viral genome into the host cell and inhibition of PARP blocks the integration of the viral genome into the host DNA. For this reason, the non-toxic PARP inhibitors can inhibit the virulent retroviruses and stop propagation of retroviruses like HIV and non-B type hepatitis.

Based of the above experimental results, it can be established that the compounds of the invention—due to their reverse transcriptase and PARP inhibitory effect—can be employed also as antiviral active substances having several points of attack.

Thus, the novel propenecarboxylic acid amidoxime derivatives can be used as active ingredients of pharmaceutical compositions. Therefore, the invention includes a pharmaceutical composition comprising an unsaturated hydroximic acid derivative of the formula I or an N-oxide or geometrical isomer(s) and/or optical isomer(s) or a pharmaceutically suitable acid addition salt and/or a quaternary derivative thereof as the active ingredient and one or more conventional carrier(s) used in pharmaceutical compositions.

The pharmaceutical composition of the invention contains, in general, 0.1–95% by weight, preferably 1–50% by weight, suitably 5–30% by weight of the active ingredient, and is suitable for the treatment of diseases based on oxygen and energy deficient states, PARP inhibition, especially autoimmune or neurodegenerative and/or viral diseases, furthermore for the prevention of toxic effects.

In connection with the invention, the term "active ingredient" includes a compound of the formula I or an N-oxide thereof or one or more geometrical and/or optical isomer(s) of the compound of the formula I or the N-oxide, a pharmaceutically suitable acid addition salt and/or a quaternary salt of the compound of the formula I or the N-oxide or a pharmaceutically suitable acid addition salt and/or quaternary salt of the isomer(s) of the compound of the formula I or the N-oxide.

The pharmaceutical composition of the invention is suitable for peroral, parenteral or rectal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinylpyrrolidone) etc.; filling agents such as lactose, glucose, starch, calcium phosphate etc.; auxiliary substances for tabletting such as magnesium stearate, talc, poly(ethylene glycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, glycerol, propylene glycol, ethanol etc.; preservatives such as methyl p-hydroxybenzoate etc. as the carrier.

Pharmaceutical compositions suitable for parenteral administration consist of sterile solutions of the active ingredient, in general.

Dosage forms listed above as well as other dosage forms are known per se, see e.g. Remington's Pharmaceutical Sciences, 18th Edition, Mack Publishing Co., Easton, USA (1990).

The pharmaceutical composition contains dosage unit, in general. A typical dose for adult patients amounts to 0.1 to 1000 mg of the compound of the formula I or an N-oxide or a pharmaceutically suitable acid addition salt and/or a quaternary derivative thereof calculated for 1 kg body weight, daily. The daily dose can be administered in one or more portions. The actual dosage depends on many factors and is determined by the doctor.

The pharmaceutical composition is prepared by admixing the active ingredient to one or more carrier(s), and converting the mixture obtained to a pharmaceutical composition in a manner known per se. Useful methods are known from the literature, e.g. Remington's Pharmaceutical Sciences mentioned above.

A preferred subgroup of the pharmaceutical composition of the invention contains a propene-carboxylic acid amidoxime derivative of the formula Ia, wherein R, R', $R_3$, $R_4$ and $R_5$ are as defined in connection with the formula Ia, or an N-oxide or geometrical isomer(s) and/or optical isomer(s) or a pharmaceutically suitable acid addition salt and/or a quaternary derivative thereof as the active ingredient.

Another preferred subgroup of the pharmaceutical composition of the invention contains a propene-carboxylic acid amidoxime derivative of the formula Ib wherein R, R', $R_3$, $R_4$, $R_5$ and X are as defined in connection with the formula Ib or an N-oxide or geometrical isomer(s) and/or optical isomer(s) or a pharmaceutically suitable acid addition salt and/or a quaternary derivative thereof as the active ingredient.

A further preferred subgroup of the pharmaceutical composition of the invention contains a propene-carboxylic acid amidoxime derivative of the formula Ic, wherein R, R', $R_4$ and $R_5$ are as defined in connection with the formula Ic, or an N-oxide or geometrical isomer(s) and/or optical isomer(s) or a pharmaceutically suitable acid addition salt and/or a quaternary derivative thereof as the active ingredient.

The invention includes a method of treatment in which a patient suffering from especially a state connected with oxygen deficit and/or energy deficit, or a disease based on PARP inhibition, especially an autoimmune or neuro-degenerative disease, and/or a viral disease, and/or a disease caused by a toxic effect is treated with a non-toxic dose of a propenecarboxylic acid amidoxime derivative of the formula I or an N-oxide or a geometrical isomer and/or optical isomer or a pharmaceutically suitable acid addition salt and/or a quaternary derivative thereof.

In addition, the invention includes the use of a propenecarboxylic acid amidoxime derivative of the formula I or an N-oxide or a geometrical isomer and/or optical isomer or a pharmaceutically suitable acid addition salt and/or a quaternary derivative thereof for the preparation of a pharmaceutical composition suitable for the treatment of a state connected with oxygen deficit and/or energy deficit, or a disease based on PARP inhibition, especially an autoimmune or neurodegenerative disease, and/or a viral disease, and/or a disease caused by a toxic effect.

The invention is further elucidated by means of the following Examples.

EXAMPLE 1

3-Styryl-4-(3-piperidinopropyl)-$\Delta^2$-1,2,4-oxadiazolin-5-one hydrochloride 0.94 g (0.005 moles) of 3-styryl-$\Delta^2$-1,2,4-oxadiazolin-5-one are dissolved in 6 ml of acetone, to the solution obtained, 1.19 g (0.006 moles) of 1-chloro-3-piperidinopropane hydrochloride, 0.76 g (0.0055 moles) of anhydrous potassium carbonate, 1 ml of methanol and 0.05 g of potassium iodide are added. The reaction mixture is heated under reflux for 20 hours, the inorganic salts are filtered, and the solution is evaporated under reduced pressure. The residual oil-like crude product is dissolved in isopropanol, the solution obtained is acidified by the addition of hydrogen chloride in isopropanol, the reaction mixture is allowed to stand in a refrigerator for a night, and the crystals precipitated are filtered. Thus, 1.05 g of the title compound are obtained. M.p.: 203–205° C.

IR (KBr) $\nu$=2550–2650 (NH$^+$), 1768 (CO), 1639 (C=N) cm$^{-1}$. $^1$H-NMR (DMSO-d$_6$) $\delta$=1.3–1.85 (6H, m, piperidin-3,4,5-CH$_2$), 2.11 (2H, m, propyl-CH$_2$), 2.82 (2H, m, piperidine-CH$_2$), 3.09 (2H, m, —CH$_2$—N), 3.36 (2H, m, piperidine-CH$_2$), 3.87 (2H, m, —O—CH$_2$), 7.12 (1H, d, Ar—CH=CH—), 7.4–7.5 (3H, m, Ar—H), 7.60 (1H, d, Ar—CH=CH), 7.8 (2H, m, ArH), 10.3 (1H, br, $^+$NH).

EXAMPLE 2

3-Styryl-4-(3-piperidino-2-hydroxipropyl)-$\Delta^2$-1,2,4-oxadiazolin-5-one hydrochloride A) 2.25 g (0.008 moles) of 3-styryl-4-(3-chloro-2-hidroxypropyl)-$\Delta^2$-1,2,4-oxadiazolin-5-one are dissolved in 10 ml of ethanol, to the solution obtained, 0.68 g (0.008 moles) of piperidine are added, the mixture is heated to 50° C. and, under stirring, a solution of 0.32 g (0.008 moles) of sodium hydroxide in 2 ml of water are added, drop by drop. The reaction mixture is stirred at 50–55° C. for further 2 hours, the crystals precipitated are filtered, dried, then dissolved in ethanol under heating, and the solution obtained is acidified by the addition of hydrogen chloride in isopropanol. The reaction mixture is allowed to stand in a refrigerator for a night, the crystals precipitated are filtered and dried. Thus, 1.09 g of the title compound are obtained. M.p.: 234–235° C. (3-Styryl-4-(3-chloro-2-hydroxypropyl)-$\Delta^2$-1,2,4-oxadiazolin-5-one used as the starting compound was prepared by the reaction of 3-styryl-$\Delta^2$-1,2,4-oxadiazolin-5-on and epichlorohydrin according to the method described in the literature [Chem. Ber., 108, 1911 (1975)].

$^1$H-NMR (DMSO-d$_6$) $\delta$=1.3–1.9 (6H, m, piperidine-3,4,5-CH$_2$), 2.9–3.6 (6H, m, 3CH$_2$), 3.8 (2H, m, propyl-1-CH$_2$), 4.35 (1H, m, CH—OH), 6.3 (1H, br, OH), 7.19 (1H, d, Ar—CH=CH), 7.37–7.47 (3H, m, Ar—H), 7.57 (1H, d, Ar—CH=CH—), 7.84 (2H, m, Ar—H), 10.25 (1H, br, $^+$NH).

B) 0.65 g (0.0027 moles) of 3-styryl-4-(2,3-epoxypropyl)-$\Delta^2$-1,2,4-oxadiazolin-5-one are dissolved in 2 ml of methanol, and, to the solution obtained, 0.24 g (0.0028 moles) of piperidine are added. The reaction mixture that becomes warm is allowed to stand for an hour. The precipitated crystals are filtered, then dissolved in isopropanol. The solution is acidified by the addition of hydrogen chloride in isopropanol. Thus, 0.38 g of the title product crystallizes which is identical with the compound obtained under section A. M.p.: 234–235° C. (3-Styryl- 4-(2,3-epoxypropyl)-$\Delta^2$-1,2,4-oxadiazolin-5-one used as the starting compound is prepared as follows: 1.5 g (0.0053 moles) of 3-styryl-4-(3-chloro-2-hydroxypropyl)-$\Delta^2$-1,2,4-oxadiazolin-5-one are dissolved in 5 ml of acetone, to the solution obtained, 0.73 g of anhydrous potassium carbonate are added, the reaction mixture is boiled under reflux for 16 hours, then filtered and evaporated under reduced pressure. Thus, 1.41 g of 3-styryl-4-(2,3-epoxypropyl)-$\Delta^2$-1,2,4-oxadiazolin-5-one are obtained in the form of oil-like matter.

C) 0.3 g (0.0016 moles) of 3-styryl-$\Delta^2$-1,2,4-oxadiazolin-5-one are dissolved in 3 ml of acetone, to the solution obtained, 0.41 g (0.0019 moles) of 3-piperidino-2-hydroxy-1-chloropropane hydrochloride, 0.48 g of anhydrous potassium carbonate, 1 ml of methanol and 0.05 g of potassium iodide are added. The reaction mixture is boiled under reflux for 40 hours, then filtered, and the solvent is distilled off under reduced pressure. The residue is dissolved in 5% aqueous hydrochloric acid, the solution is filtered and the filtrate is made alkaline by the addition of 10% aqueous sodium hydroxide solution. The product precipitated is extracted with chloroform, the solution is dried over anhydrous sodium sulfate, the solvent is evaporated under reduced pressure. The residue is dissolved in isopropanol, and the solution obtained is acidified by the addition of hydrogen chloride in isopropanol. 0.18 g of product crystallizes which is identical with the title product prepared under section A. M.p.: 234–235° C.

EXAMPLE 3

3-Styryl-4-(3-pyrrolidino-2-hydroxypropyl)-$\Delta^2$-1,2,4-oxadiazolin-5-one-hydrochloride 8.4 g (0.03 moles) of 3-styryl-4-(3-chloro-2-hydroxypropyl)-$\Delta^2$-1,2,4-oxadiazolin-5-one are dissolved in 30 ml of ethanol, to the solution obtained, 2.55 g (0.036 moles) of pyrrolidine, then, at 60° C., 1.2 g (0.03 moles) of sodium hydroxide in 8 ml of water are added, drop by drop, under stirring. The reaction mixture is stirred for a further hour at 60° C.-on, then the ethanol is distilled off under reduced pressure. The residue is acidified by the addition of concentrated aqueous hydrochloric acid, the solution is treated with charcoal, filtered, and made alkaline by the addition of 2N aqueous sodium hydroxide solution. The precipitated oily matter is extracted with chloroform, the organic solution is dried over anhydrous sodium sulfate, filtered, and evaporated. The residue is dissolved in isopropanol, the solution obtained is acidified by the addition of hydrogen chloride in isopropanol. The crystals are filtered and dried. Thus, 1.8 g of the title compound are obtained.

M.p.: 188–189° C. $^1$H-NMR (DMSO-d$_6$) δ=1.8–2.0 (4H, m, pyrrolidine-3,4-CH$_2$), 3.06–3.55 (6H, m, 3CH$_2$), 3.82 (2H, d, propyl-1-CH$_2$), 4.21 (1H, m, —C$\underline{H}$—OH), 6.25 (1H, d, —O$\underline{H}$), 7.14 (1H, d, Ar—CH=C$\underline{H}$—), 7.4–7.5 (3H, m, Ar—H), 7.58 (1H, d, Ar—C$\underline{H}$=CH—), 7.82 (2H, m, ArH), 10.3 (1H, br, $^+$NH).

EXAMPLE 4

3-Styryl-4-(3-hexamethyleneimino-2-hydroxypropyl)-$\Delta^2$-1,2,4-oxadiazolin-5-one hydrochloride 2.8 g (0.01 moles) of 3-styryl-4-(3-chloro-2-hydroxypropyl)-$\Delta^2$-1,2,4-oxadiazolin-5-one are reacted with 1.19 g (0.012 moles) of hexamethyleneimine according to the method described in Example 3. The hydrochloride is precipitated in an isopropanolic solution by the addition of hydrogen chloride in isopropanol. Thus, 1.0 g of the title compound are obtained.

M.p.: 202–203° C. $^1$H-NMR (CDCl$_3$+DMSO-d$_6$) δ=1.6–2.0 (8H, m, hexamethyleneimine-3,4,5,6-CH$_2$), 3.1–3.6 (6H, m, 3CH$_2$), 3.8 (2H, m, propyl-1-CH$_2$), 4.35 (1H, m, —C$\underline{H}$—OH), 6.21 (1H, d, OH), 7.11 (1H, d, Ar—CH=C$\underline{H}$—), 7.4 (3H, m, Ar—H), 7.57 (1H, d, Ar—C$\underline{H}$=CH—), 7.77 (2H, m, Ar—H), 10.0 (1H, br, $^+$NH).

EXAMPLE 5

3-Styryl-4-(3-morpholino-2-hydroxypropyl)-$\Delta^2$-1,2,4-oxadiazolin-5-one hydrochloride 4.2 g (0.015 moles) of 3-styryl-4-(3-chloro-2-hydroxypropyl)-$\Delta^2$-1,2,4-oxadiazolin-5-one are reacted with 1.6 g (0.018 moles) of morpholine according to the method described in Example 3. The hydrochloride is precipitated in an ethanolic solution by the addition of hydrogen chloride in isopropanol. Thus, 0.67 g of the title compound are obtained. M.p.: 232–234° C.

$^1$H-NMR (DMSO-d$_6$) δ=3.1–3.55 (6H, m, morpholin-3,5-CH$_2$, propyl-3-CH$_2$), 3.8–4.0 (6H, m, morpholine-2,6-CH$_2$, propyl-1-CH$_2$), 4.37 (1H, m, —C$\underline{H}$—OH), 6.3 (1H, br, OH), 7.12 (1H, d, Ar—CH=C$\underline{H}$—), 7.4 (3H, m, ArH), 7.6 (1H, d, Ar—C$\underline{H}$=CH—), 7.8 (2H, m, ArH), 10.6 (1H, br, $^+$NH).

EXAMPLE 6

3-Styryl-4-[3-(tert.-butylamino)-2-hydroxypropyl]-$\Delta^2$-1,2,4-oxadiazolin-5-one hydrochloride 6.6 g (0.024 moles) of 3-styryl-4-(3-chloro-2-hidroxypropyl)-$\Delta^2$-1,2,4-oxadiazolin-5-one are reacted with 2.63 g (0.036 moles) of tert.-butylamine according to the method described in Example 3. The hydrochloride is precipitated in an isopropanolic solution by the addition of hydrogen chloride in isopropanol. Thus, 1.8 g of the title compound are obtained.

M.p.: 244–246° C. $^1$H-NMR (DMSO-d$_6$) δ=1.3 (9H, s, tert.-butyl), 2.9–3.15 (2H, m, propyl-3-CH$_2$), 3.85 (2H, m, propyl-1-CH$_2$), 4.15 (1H, m, C$\underline{H}$—OH), 6.08 (1H, d, OH), 7.12 (1H, d, Ar—CH=C$\underline{H}$—), 7.40 (3H, m, Ar—H), 7.55 (1H, d, Ar—C$\underline{H}$=CH), 7.8 (2H, m, Ar—H), 8.55 (1H, br, NH), 8.85 (1H, br, NH).

EXAMPLE 7

3-Styryl-4-[3-(4-methyl-1-piperazinyl)-2-hydroxypropyl]-$\Delta^2$-1,2,4-oxadiazolin-5-one dihydrochloride 8.4 g (0.03 moles) of 3-styryl-4-(3-chloro-2-hydroxypropyl)-$\Delta^2$-1,2,4-oxadiazolin-5-one are reacted with 3.6 g (0.036 moles) of N-methylpiperazine according to the method described in Example 3. The hydrochloride is precipitated in an isopropanolic solution by the addition of hydrogen chloride in isopropanol. Thus, 2.08 g of the title compound are obtained.

M.p.: 206–208° C. $^1$H-NMR (DMSO-d$_6$) δ=2.77 (3H, s, CH$_3$), 3.0–3.1 (2H, m, propyl-3-CH$_2$), 3.6 (8H, m, piperazine-CH$_2$), 3.8 (2H, m, propyl-1-CH$_2$), 4.23 (1H, m, —C$\underline{H}$—OH), 6.2 (1H, br, OH), 7.03 (1H, d, Ar—CH=C$\underline{H}$—), 7.4 (3H, m, Ar—H), 7.58 (1H, d, Ar—C$\underline{H}$=CH—), 7.77 (2H, m, ArH), 11.8 (2H, br, 2×$^+$NH).

EXAMPLE 8

3-Styryl-4-[3-(1,2,3,4-tetrahydro-2-isoquinolyl)-2-hydroxypropyl]-Δ²-1,2,4-oxadiazolin-5-one hydrochloride 2.8 g (0.01 moles) of 3-styryl-4-(3-chloro-2-hydroxypropyl)-Δ²-1,2,4-oxadiazolin-5-one are reacted with 1.6 g (0.012 moles) of 1,2,3,4-tetrahydroisoquinoline according to the method described in Example 3. The hydrochloride is precipitated in an isopropanolic solution by the addition of hydrogen chloride in isopropanol. Thus, 0.83 g of the title compound are obtained, M.p.: 208–210° C.

$^1$H-NMR (DMSO-d$_6$) δ=3.0–3.6 (8H, m, isoquinoline-CH$_2$, propyl-3-CH$_2$), 3.84 (2H, m, propyl-1-CH$_2$), 4.4 (1H, m, —CH—OH), 6.3 (1H, br, OH), 7.13 (1H, d, Ar—C H—CH—), 7.2–7.5 (7H, m, ArH), 7.60 (1H, d, Ar—C H=CH—), 7.8 (2H, m, Ar—H), 10.6 (1H, br, $^+$NH).

EXAMPLE 9

3-Styryl-4-[3-(2,6-dimethylanilino)-2-hydroxypropyl]-Δ²-1,2,4-oxadiazolin-5-one hydrochloride 8.4 g (0.03 moles) of 3-styryl-4-(3-chloro-2-hydroxypropyl)-Δ²-1,2,4-oxadiazolin-5-one are reacted with 4.36 g (0.036 moles) of 2,6-dimethylaniline, instead of ethanol in 50 ml of methanol, according to the method described in Example 3. The hydrochloride is precipitated in an isopropanolic solution by the addition of hydrogen chloride in isopropanol, then recrystallized from a mixture of one volume of isopropanol and one volume of ethanol. Thus, 1.62 9 of the title compound are obtained. M.p.: 182–184° C.

$^1$H-NMR (DMSO-d$_6$) δ=2.44 (6H, s, CH$_3$), 3.16–3.53 (2H, m, propyl-3-CH$_2$), 3.86 (2H, m, propyl-1-CH$_2$), 4.21 (1H, m, CH—OH), 6.0 (1H, br, OH), 7.10 (1H, d, Ar—CH=CH—), 7.14 (3H, m, ArH), 7.4–7.5 (3H, m, ArH), 7.59 (1H, d, Ar—CH=CH—), 7.78 (2H, m, ArH), 9.0 (2H, br, $^+$NH$_2$).

EXAMPLE 10

3-(3,4-Dimethoxystyryl)-4-(3-piperidino-2-hydroxypropyl)-Δ²-1,2,4-oxadiazolin-5-one hydrochloride 3.4 g (0.01 moles) of 3-(3,4-dimethoxystyryl)-4-(3-chloro-2-hydroxypropyl)-Δ²-1,2,4-oxadiazolin-5-one are reacted with 1.02 g (0.012 moles) of piperidine according to the method described in Example 3. The hydrochloride is precipitated in an ethanolic solution by the addition of hydrogen chloride in isopropanol. Thus, 1.8 g of the title compound are obtained.

M.p.: 187–188° C. $^1$H-NMR (CDCl$_3$+DMSO-d$_6$) δ=1.4–2.0 (6H, m, piperidine-3,4,5-CH$_2$), 3.18–3.31 (6H, m, piperidine-2,6-CH$_2$, propyl-3-CH$_2$), 3.85–3.92 (2H, m, propyl-1-CH$_2$), 3.89 (3H, s, —OCH$_3$), 3.96 (3H, s, —OCH$_3$), 4.45 (1H, m, CH—OH), 6.27 (1H, br, OH), 6.93 (1H, m, ArH), 6.98 (1H, d, Ar—CH=CH—), 7.21 (1H, m, ArH), 7.42 (1H, m, ArH), 7.48 (1H, d, Ar—CH=CH—), 9.8 (1H, br, $^+$NH).

3-(3,4-Dimethoxystyryl)-4-(3-chloro-2-hydroxypropyl)-Δ²-1,2,4-oxadiazolin-5-one used as the starting compound was prepared from 3-(3,4-dimethoxystyryl)-Δ²-1,2,4-oxadiazolin-5-one with epichlorohydrin according to the method known from the literature [Chem. Ber., 108, 1911 (1975)]

EXAMPLE 11

3-Styryl-4-[3-(1-methyl-4-piperazinyl)-2-hydroxypropyl]-Δ²-1,2,4-oxadiazolin-5-one dihydrochloride 2.0 g (0.0059 moles) of 3-(3,4-dimethoxystyryl)-4-(3-chloro-2-hydroxypropyl)-Δ²-1,2,4-oxadiazolin-5-one are reacted with 0.71 g (0.0071 moles) of N-methylpiperazine according to the method described in Example 3. The hydrochloride is precipitated in an isopropanolic solution by the addition of hydrogen chloride in isopropanol. Thus, 0.8 g of the title compound are obtained. M.p.: 192–193° C.

$^1$H-NMR (DMSO-d$_6$) δ=2.8 (3H, s, N—CH$_3$), 3.2–3.8 (10H, m, piperazine-CH$_2$, propyl-3-CH$_2$), 3.80 (3H, s, methoxy), 3.83 (2H, m, propyl-1-CH$_2$), 3.86 (3H, s, OCH$_3$), 4.31 (1H, m, —CH—OH), 6.3 (1H, br, OH), 7.0 (1H, m, ArH), 7.03 (1H, d, Ar—CH=CH—), 7.30 (1H, m, ArH), 7.50 (1H, m, ArH), 7.51 (1H, d, Ar—CH=CH—), 11.8 (2H, br, 2×$^+$NH).

EXAMPLE 12

N-(3-Piperidino-2-hydroxypropyl)cinnamic acid amidoxime

To 1.91 g (0.006 moles) of 3-styryl-4-(3-piperidino-2-hydroxypropyl)-Δ²-1,2,4-oxadiazolin-5-one prepared according to the method described in Example 2, 10 ml of ethanol and 10 ml of 10% aqueous sodium hydroxide solution are added, and the reaction mixture is boiled under reflux for 2 hours. The ethanol is evaporated under reduced pressure, the pH value of the residue is adjusted to 8 by the addition of hydrochloric acid. From the partly solid product the aqueous phase is decanted, the residue is dissolved in methanol. On dilution with water, 0.79 g of the title compound crystallizes. M.p.: 114–115° C.

$^1$H-NMR (DMSO-d$_6$) δ=1.7–1.9 (6H, m, piperidine-3,4,5-CH$_2$), 2.1–2.3 (6H, m, piperidine-2,6-CH$_2$, propyl-3-CH$_2$), 3.2–3.33 (2H, m, propyl-1-CH$_2$), 3.83 (1H, m, C H—OH), 5.6 (1H, br, OH), 6.55 (1H, d, Ar—CH=CH—), 7.15 (1H, d, Ar—CH=CH—), 7.8–7.32 (3H, m, ArH), 7.44 (2H, m, ArH).

EXAMPLE 13

N-(3-Morpholino-2-hydroxypropyl)cinnamic acid amidoxime dihydrogen maleate

To 2.76 g (0.0075 moles) of 3-styryl-4-(3-morpholino-2-hydroxypropyl)-Δ²-1,2,4-oxadiazolin-5-one prepared according to the method described in Example 5, 10 ml of ethanol és 10 ml of 10% sodium hydroxide solution are added, and the reaction mixture is boiled under reflux for 2 hours. The ethanol is evaporated under reduced pressure, the pH of the residue is adjusted to 8 by the addition of hydrochloric acid. The oil-like product precipitated is extracted with dichloromethane, the organic solution is dried over anhydrous sodium sulfate, the solvent is evaporated. The maleate is precipitated in an acetone solution by the addition of maleic acid. Thus, 1.1 g of the title compound are obtained. M.p.: 128–130° C.

$^1$H-NMR (CDCl$_3$+DMSO-d$_6$) δ=2.8–3.2 (6H, morpholine-3,5-CH$_2$, propyl-3-CH$_2$—), 3.3–3.8 (6H, m, morpholine-2,6-CH$_2$, propyl-1-CH$_2$), 4.10 (1H, m, CH—OH), 6.05 (4H, s, maleic acid CH), 6.75 (1H, d, Ar—CH=CH—), 7.30 (1H, d, Ar—CH=CH—), 7.3 (3H, m, ArH), 7.50 (2H, m, ArH).

EXAMPLE 14

N-[3-(1-Methyl-4-piperazinyl)-2-hydroxypropyl] cinnamic acid amidoxime trihydrogen maleate 1.17 g (0.0025 moles) of 3-styryl-4-[3-(4-methyl-1-piperazinyl)-2-hydroxypropyl]-$\Delta^2$-1,2,4-oxadiazolin-5-one prepared according to the method described in Example 7 are reacted with sodium hydroxide according to the method described in Example 13. The maleate is precipitated in an acetone solution by the addition of maleic acid. Thus, 0.63 g of the title compound are obtained. M.p.: 142–143° C.

$^1$H-NMR (DMSO-d$_6$) δ=2.7 (3H, s, CH$_3$), 2.5–3.2 (10H, m, piperazine-CH$_2$, propyl-3-CH$_2$), 3.31–3.42 (2H, m, propyl-1-CH$_2$), 3.81 (1H, m, CH—OH), 6.14 (6H, s, maleic acid CH), 6.90 (1H, d, Ar—CH=CH—), 7.28 (1H, d, Ar—CH=CH), 7.4 (3H, m, ArH), 7.65 (2H, m, ArH).

EXAMPLE 15

N-(3-Morpholino-2-hydroxypropyl)-3,4-dimethoxycinnamic acid amidoxime 3.91 g (0.01 moles) of 3-(3,4-dimethoxystyryl)-4-(3-morpholino-2-hydroxypropyl)-$\Delta^2$-1,2,4-oxadiazolin-5-one are reacted with sodium hydroxide according to the method described in Example 13. Thus, 1.2 g of the title compound are obtained as an oil-like product.

$^1$H-NMR (DMSO-d$_6$) δ=3.18–3.35 (6H, morpholine-3,5-CH$_2$, propyl-3-CH$_2$), 3.60 (2H, m, propyl-1-CH$_2$), 3.82 (3H, s, OCH$_3$), 3.86 (3H, s, OCH$_3$), 3.92 (4H, m, morpholine-2, 6-CH$_2$), 4.34 (1H, m, —CH—OH), 6.3 (1H, br, —CH—OH), 6.98 (1H, d, Ar—CH=CH—), 7.02 (1H, m, Ar-3H), 7.24 (1H, m, Ar-2H), 7.35 (1H, d, Ar—CH=CH—), 7.40 (1H, m, Ar-6H).

EXAMPLE 16

3-Styryl-6-(piperidinomethyl)-4H-5,6-dihydro-1,2,4-oxadiazine

To 1.65 g (0.0043 moles) of 3-styryl-4-(3-piperidino-2-chloropropyl)-$\Delta^2$-1,2,4-oxadiazolin-5-one hydrochloride, a mixture of 33 ml of ethanol and 33 ml of 2N aqueous sodium hydroxide solution is added, the reaction mixture is boiled under reflux for 30 minutes under stirring, then evaporated under reduced pressure, and the residue is suspended in 10 ml of water. The crystals are filtered, washed with water, and dried. Thus, 1.06 g of the title compound are obtained. M.p.: 147–149° C.

$^1$H-NMR (DMSO-d$_6$) δ=1.3–1.7 (6H, m, piperidine-3,4,5-CH$_2$), 2.3–2.7 (6H, m, piperidine-2,6-CH$_2$, 6-CH$_2$), 3.25–3.6 (2H, m, oxadiazine-5-CH$_2$), 3.95 (1H, m, oxadiazine-6-CH), 5.0 (1H, br, oxadiazine-4-NH), 6.5 (1H, d, Ar—CH=CH—), 6.9 (1H, d, Ar—CH=CH—), 7.2–7.5 (5H, m, ArH).

3-Styryl-4-(3-piperidino-2-chloropropyl)-$\Delta^2$-1,2,4-oxadiazolin-5-one hydrochloride used as the starting compound is prepared from 3-styryl-4-(3-piperidino-2-hydroxypropyl)-$\Delta^2$-1,2,4-oxadiazolin-5-one (prepared as described in Example 2) with thionyl chloride according to the method known from the literature [Chem. Ber., 108, 1911 (1975)].

EXAMPLE 17

3-Styryl-6-morpholino-methyl-4H-5,6-dihydro-1,2,4-oxadiazine dihydrogen maleate To 1.5 g (0.0039 moles) of 3-styryl-4-(3-morpholino-2-chloropropyl)-$\Delta^2$-1,2,4-oxadiazolin-5-one hydrochloride, 9 ml of ethanol and 9 ml of 10% aqueous sodium hydroxide solution are added, and the reaction mixture is boiled under reflux for half an hour. The ethanol is evaporated under reduced pressure, the residue is acidified with 5% hydrochloric acid. The solution obtained is treated with charcoal, filtered, and made alkaline by the addition of 10% aqueous sodium hydroxide solution. The precipitated oily matter is extracted with chloroform, the organic phase is dried over anhydrous sodium sulfate, filtered, and the solvent is evaporated. The residue is dissolved in ethyl acetate, and a solution of 0.66 g of maleic acid in ethyl acetate is added. Thus, 1.0 g of the title product is obtained. M.p.: 137° C.

$^1$H-NMR (DMSO-d$_6$) δ=3.1–3.44 (8H, m, 5-CH$_2$, 6-CH$_2$, morpholine-3-és-5-CH$_2$), 3.83 (4H, m, morpholine-2- and -6-CH$_2$), 4.08 (1H, m, 6-CH), 6.18 (4H, s, maleic acid CH), 6.43 (1H, d, Ar—CH=CH—), 7.25 (1H, br, 4H), 7.33–7.51 (5H, m, 5 Ar—H), 13–14 (br, maleic acid OH).

3-Styryl-4-(3-morpholino-2-chloropropyl)-$\Delta^2$-1,2,4-oxadiazolin-5-one hydrochloride used as the starting compound is prepared from 3-styryl-4-(3-morpholino-2-hydroxypropyl)-$\Delta^2$-1,2,4-oxadiazolin-5-one hydrochloride (prepared according to Example 5) by heating it with thionyl chloride, then evaporating the reaction mixture.

EXAMPLE 18

3-Styryl-6-(1,2,3,4-tetrahydro-2-isoquinolyl)-methyl-4H-5,6-dihydro-1,2,4-oxadiazine dihydrogen maleate To 1.1 g (0.0025 moles) of 3-styryl-4-[3-(1,2,3,4-tetrahydro-2-isoquinolyl)-2-chloropropyl-$\Delta^2$-1,2,4-oxadiazolin-5-one hydrochloride, 8 ml of ethanol and 8 ml of 10% sodium hydroxide are added, and the reaction mixture is boiled under reflux for half an hour. The ethanol is evaporated under reduced pressure, and the residue is dissolved in 5% hydrochloric acid. The solution is treated with charcoal, filtered, made alkaline by the addition of 10% aqueous sodium hydroxide solution, and extracted with ethyl acetate. The combined ethyl acetate solutions are dried over anhydrous sodium sulfate, filtered, and evaporated. The residue is dissolved in ethyl acetate, and, to the solution obtained, 0.36 g of maleic acid are added. Thus, 0.55 g of the title compound are obtained. M.p.: 151–153° C.

$^1$H-NMR (DMSO-d$_6$) δ=3.10 (2H, m, isoquinoline-4-CH$_2$), 3.15–3.50 (2H, m, oxadiazine-5-CH$_2$), 3.28–3.39 (2H, m, oxadiazine-6-CH$_2$—N=), 3.44–3.6 (2H, m, isoquinoline-3-CH$_2$), 4.2 (1H, m, oxadiazine-6-CH), 4.4 (2H, s, isoquinoline-1-CH$_2$), 6.13 (4H, s, maleic acid CH), 6.44 (1H, d, Ar—CH=CH—), 7.15 (1H, d, Ar—CH=CH—), 7.2–7.33 (4H, m, isoquinoline Ar—H), 7.33–7.52 (5H, m, phenyl Ar—H).

EXAMPLE 19

3-(3,4-Dimethoxystyryl)-4-[3-(tert.-butylamino)-2-hydroxypropyl]-Δ²-1,2,4-oxadiazolin-5-one hydrochloride 8.54 g (0.025 moles) of 3-(3,4-dimethoxystyryl)-4-(3-chloro-2-hydroxypropyl)-Δ²-1,2,4-oxadiazolin-5-one are dissolved in 40 ml of acetone and, to the solution obtained, 3.46 g (0.025 moles) of anhydrous potassium carbonate are added. The reaction mixture is boiled under reflux for 6 hours, then cooled, the inorganic salts are removed by filtration, the solvent is evaporated under reduced pressure. The evaporation residue is rubbed with 25 ml of methanol to induce crystallization. Thus, 6.5 g of 3-(3,4-dimethoxystyryl)-4-(2,3-epoxypropyl)-Δ²-1,2,4-oxadiazolin-5-one are obtained. M.p.: 113–115° C.

To 3.04 g (0.01 moles) of 3-(3,4-dimethoxystyryl)-4-(2,3-epoxypropyl)-Δ²-1,2,4-oxadiazolin-5-one, 15 ml of methanol and 0.73 g (0.01 moles) of tert.-butylamine are added, the reaction mixture is boiled under reflux for 4 hours, then the solvent is evaporated under reduced pressure. The residue is dissolved in 10 ml of 5% hydrochloric acid, and the solution is decanted from the residue that did not dissolve. The aqueous solution is made alkaline by the addition of 10% aqueous sodium hydroxide solution, the formed oil is dissolved in dichloromethane, the solution is dried over anhydrous sodium sulfate, filtered, and the solvent is evaporated under reduced pressure. 1.7 g of oil-like product are obtained the hydrochloride of which is precipitated from ethanol by the addition of isopropanol containing hydrogen chloride. Thus, 1.0 g of the title compound are obtained. M.p.: 225–227° C.

$^1$H-NMR (DMSO-$d_6$) δ=1.3 (9H, s, 3×CH$_3$), 2.93–3.17 (2H, m, propyl-3-CH$_2$), 3.80 (3H, s, —OCH$_3$), 3.85 (3H, s, —OCH$_3$), 3.9 (2H, d, propyl-1-CH$_2$), 4.16 (1H, m, —CH—OH), 6.12 (1H, d, —OH), 7.03 (1H, d, Ar—CH=CH—), 7.51 (1H, d, Ar—CH=CH—), 7.00 (1H, m, ArH), 7.29 (1H, m, ArH), 7.49 (1H, m, ArH), 8.58 (1H, br, NH), 8.86 (1H, br, NH).

EXAMPLE 20

3-(3,4-Dimethoxystyryl)-4-(3-morpholino-2-hydroxypropyl)-Δ²-1,2,4-oxadiazolin-5-one hydrochloride 3.04 g (0.01 moles) of 3-(3,4-dimethoxystyryl)-4-(2,3-epoxypropyl)-Δ²-1,2,4-oxadiazolin-5-one (prepared as described in Example 19) are reacted with 0.96 g (0.011 moles) of morpholine in the manner described in Example 19. Thus, 0.8 g of the title compound are obtained. M.p.: 228–230° C.

$^1$H-NMR (DMSO-$d_6$) δ=3.2–3.34 (6H, m, morpholin-3,5-CH$_2$, propyl-3-CH$_2$), 3.82 (3H, s, —OCH$_3$), 3.86 (2H, d, propyl-1-CH$_2$), 3.88 (3H, s, —OCH$_3$), 3.90 (4H, m, morpholin-2,6-CH$_2$), 4.43 (1H, m, —CH—OH), 6.4 (1H, br, —OH), 7.0 (1H, d, ArH), 7.03 (1H, d, Ar—CH=CH—), 7.29 (1H, m, ArH), 7.48 (1H, m, ArH), 7.50 (1H, d, Ar—CH=CH—), 10.7 (1H, br, +NH).

EXAMPLE 21

N-[3-(2,6-Dimethylanilino)-2-hydroxypropyl]-cinnamic acid amidoxime

The procedure described in Example 12 is followed with the difference that 1.5 g (0.004 moles) of 3-styryl-4-[3-(2,6-dimethylanilino)-2-hydroxypropyl]-Δ²-1,2,4-oxadiazolin-5-one (prepared according to Example 9) are used as the starting compound. Thus, 0.55 g of the title compound are obtained.

M.p.: 143–144° C. $^1$H-NMR (DMSO-$d_6$) δ=2.20 (6H, s, 2×CH$_3$), 2.82–3.03 (2H, m, propyl-3-CH$_2$), 3.15–3.27 (2H, m, propyl-1-CH$_2$), 3.64 (1H, m, —CH—OH), 3.80 (1H, m, NH-aniline), 5.15 (1H, br, —CH—OH), 5.58 (1H, br, NH-amidoxime), 6.68 (1H, d, Ar—CH=CH—), 6.69 (1H, m, ArH), 6.90 (2H, m, ArH), 7.01 (1H, d, Ar—CH=CH—), 7.25–7.55 (5H, m, ArH), 9.57 (1H, S, =N—OH).

EXAMPLE 22

N-(3-Pyrrolidino-2-hydroxypropyl)-cinnamic acid amidoxime

The procedure described in Example 12 is followed with the difference that 1.23 g (0.0035 moles) of 3-styryl-4-(3-pyrrolidino-2-hydroxypropyl)-Δ²-1,2,4-oxadiazolin-5-one hydrochloride (prepared according to Example 3) are used as the starting compound. Thus, 0.65 g of the title compound are obtained. M.p.: 139–141° C. (from 96% ethanol).

$^1$H-NMR (CDCl$_3$+DMSO-$d_6$) δ=1.75 (4H, m, pyrrolidin-3,4-CH$_2$), 2.50–2.64 (6H, m, pyrrolidin-2,5-CH$_2$, propyl-3-CH$_2$), 3.2–3.35 (2H, m, propyl-1-CH$_2$), 3.75 (1H, m, CH—OH), 5.6 (1H, t, NH), 6.58 (1H, d, Ar—CH=CH—), 7.08 (1H, d, Ar—CH=CH—), 7.25–7.45 (5H, m, Ar—H), 9.0 (1H, br, =N—OH).

What is claimed is:

1. An oxadiazoline derivative of the formula

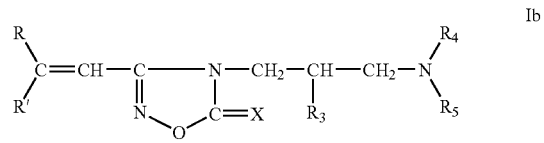

Ib

R represents a $C_{1-20}$ alkyl group, a phenyl group which latter is optionally substituted by 1–3 substituents, wherein the substituents are independently selected from the group consisting of a halo atom, a $C_{1-2}$ alkyl group, a $C_{1-2}$ alkoxy group, an amino group, a ($C_{1-4}$ alkyl)amino group, a di($C_{1-4}$ alkyl)amino group, a (C1–4 alkanoyl)amino group, a 5-membered saturated or unsaturated heterocyclic group containing one or two nitrogen atom(s) or a sulphur atom as the heteroatom and said heterocyclic group is optionally fused with one or more benzene ring(s) and/or one or more heterocyclic group(s) and a 6-membered saturated or unsaturated heterocyclic group containing one or two nitrogen atom(s) or a sulphur atom as the heteroatom and said heterocyclic group is optionally fused with one or more benzene ring(s) and/or one or more heterocyclic group(s);

R' is a hydrogen atom, or R forms together with R' a $C_{5-7}$ cycloalkyl group optionally fused with a benzene ring;

$R_4$ and $R_5$ represent, independently, a hydrogen atom, a $C_{1-5}$ alkyl group, a $C_{1-5}$ alkanoyl group or a phenyl group which latter is optionally substituted by 1–3 substituents independently selected from the group consisting of a halo atom, a $C_{1-2}$ alkyl group and a $C_{1-2}$ alkoxy group, or $R_4$ and $R_5$ form together with the adjacent nitrogen atom a 5- or 6-membered saturated or unsaturated heterocyclic group that may contain a further atom selected from the group consisting of a nitrogen atom, an oxygen atom and a sulphur atom as the heteroatom, said 5- or 6-membered saturated or unsaturated heterocyclic group optionally being fused with a benzene ring, and the heterocyclic group and/or the benzene ring may bear one or two substituents independently selected from the group consisting of a halo atom, a $C_{1-2}$ alkyl group and a $C_{1-2}$ alkoxy group;

$R_3$ represents a hydrogen atom, a halo atom, a hydroxy group, a $C_{1-5}$ alkoxy group, a $C_{1-5}$ alkylthio group, a $C_{1-20}$ alkanoyloxy group, a $C_{3-22}$ alkenoyloxy group containing one or more double bonds, a methylsulfonyloxy group, a benzenesulfonyloxy group or a toluenesulfonyloxy group; and X is an oxygen atom or a sulfur atom;

and N-oxides, geometrical isomers, optical isomers and pharmaceutically suitable acid addition salts and quaternary ammonium derivatives thereof.

2. A process for the preparation of an oxadiazoline derivative of the formula Ib and N-oxides, pharmaceutically suitable acid addition salts and quaternary ammonium derivatives thereof according to claim 1, comprising:

a) for the preparation of an oxadiazoline derivative of the formula Ib, wherein $R_3$ represents a hydrogen atom, X is an oxygen atom, R represents a $C_{1-20}$ alkyl group, a phenyl group which latter is optionally substituted by 1–3 substituents, wherein the substituents are independently selected from the group consisting of a halo atom, a $C_{1-2}$ alkyl group, a $C_{1-2}$ alkoxy group, an amino group, a ($C_{1-4}$ alkyl)amino group, a di($C_{1-4}$ alkyl)amino group, a ($C_{1-4}$ alkanoyl)amino group, a 5-membered saturated or unsaturated heterocyclic group containing one or two nitrogen atom(s) or a sulphur atom as the heteroatom and said heterocyclic group is optionally fused with one or more benzene ring(s) and/or one or more heterocyclic group(s) and a 6-membered saturated or unsaturated heterocyclic group containing one or two nitrogen atom(s) or a sulphur atom as the heteroatom and said heterocyclic group is optionally fused with one or more benzene ring(s) and/or one or more heterocyclic group(s);

R' is a hydrogen atom, or R forms together with R' a $C_{5-7}$ cycloalkyl group optionally fused with a benzene ring;

$R_4$ and $R_5$ represent, independently, a hydrogen atom, a $C_{1-5}$ alkyl group, a $C_{1-5}$ alkanoyl group or a phenyl group which latter is optionally substituted by 1–3 substituents independently selected from the group consisting of a halo atom, a $C_{1-2}$ alkyl group and a $C_{1-2}$ alkoxy group, or $R_4$ and $R_5$ form together with the adjacent nitrogen atom a 5- or 6-membered saturated or unsaturated heterocyclic group that may contain a further atom selected from the group consisting of a nitrogen atom, an oxygen atom and a sulphur atom as the heteroatom, said 5- or 6-membered saturated or unsaturated heterocyclic group optionally being fused with a benzene ring, and the heterocyclic group and/or the benzene ring may bear one or two substituents independently selected from the group consisting of a halo atom, a $C_{1-2}$ alkyl group and a $C_{1-2}$ alkoxy group;

a $\Delta^2$-1,2,4-oxadiazoline derivative of the formula

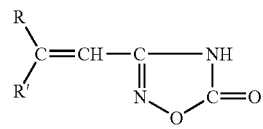

III wherein R and R' are as stated above, is reacted with an aminoalkyl halide of the formula

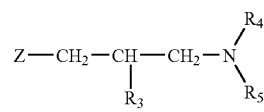

IV wherein Z is a halo atom, $R_3$, $R_4$ and $R_5$ are as stated above; or b) for the preparation of an oxadiazoline derivative of the formula Ib, wherein $R_3$ represents a hydrogen atom or a hydroxy group, X is an oxygen atom, R, R', $R_4$ and $R_5$ are as defined as above in a), a $\Delta^2$-1,2,4-oxadiazoline derivative of the formula III, wherein R and R' are as stated above in a), is reacted with a 1,3-dihalopropane of the formula

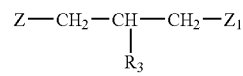

V wherein Z and $Z_1$ represent, independently, a halo atom, $R_3$ is as stated above in a), and the obtained $\Delta^2$-1,2,4-oxadiazolinylalkyl halide of the formula

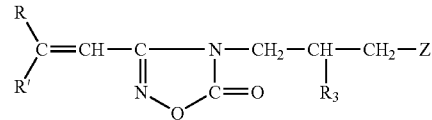

VI wherein R, R', $R_3$ and Z are as defined above in a), is reacted with an amine of the formula

VII wherein $R_4$ and $R_5$ are as defined above in a); or c) for the preparation of an oxadiazoline derivative of the formula Ib, wherein $R_3$ represents a hydroxy group, X is an oxygen atom, R, R', $R_4$ and $R_5$ are as defined above in a), a $\Delta^2$-1,2,4-oxadiazoline derivative of the formula III, wherein R and R' are as stated above in a), is reacted with epichlorohydrin, and the formed $\Delta^2$-1,2,4-oxadiazolinylalkyl chloride of the formula

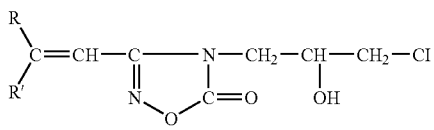

VIII wherein R and R' are as stated above in a), is reacted with an amine of the formula VII, wherein $R_4$ and $R_5$ are as defined above in a); or d) for the preparation of an oxadiazoline derivative of the formula Ib, wherein $R_3$ represents a hydroxy group, X is an oxygen atom, R, R', $R_4$ and $R_5$ are as defined above in a), a $\Delta^2$-1,2,4-oxadiazolinylalkyl chloride of the formula VIII, wherein R and R' are as stated above in a), is reacted with an acid binding agent, and the formed epoxide of the formula

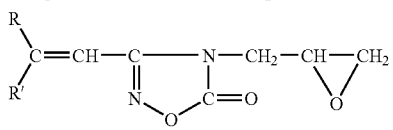

IX wherein R and R' are as stated above in a), is reacted with an amine of the formula VII, wherein $R_4$ and $R_5$ are as stated above in a); or e) for the preparation of an oxadiazoline derivative of the formula Ib, wherein $R_3$ represents a hydrogen atom or a hydroxy group, X is an oxygen atom or a sulfur atom, R, R', $R_4$ and $R_5$ are as defined above in a), a propenecarboxylic acid amidoxime derivative of the formula Ia,

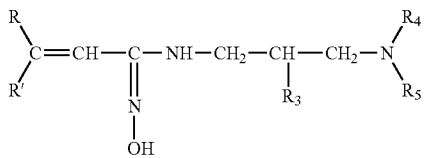

Ia wherein R, R', $R_3$, $R_4$ and $R_5$ are as defined above in a), is reacted with a carbonic acid derivative of the formula X

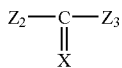

X wherein X (double-bonded to C) is an oxygen atom or a sulfur atom, $Z_2$ and $Z_3$ represent, independently, a halo atom, a $C_{1-4}$ alkoxy group or a $C_{1-4}$ alkylmercapto group;

if desired, an obtained compound of the formula Ib, wherein $R_3$ represents a hydroxy group, R, R', $R_4$ and $R_5$ are as defined above in a), and X is a oxygen atom or a sulfur atom, is reacted with a halogenating agent to obtain a compound of the formula Ib, wherein $R_3$ is a halo atom; or if desired, an obtained compound of the formula Ib, wherein $R_3$ represents a hydroxy group, R, R', $R_4$ and $R_5$ are as defined above in a), and X is an oxygen atom or a sulfur atom, is reacted with a $C_{1-20}$ alkanecarboxylic halide or a $C_{3-22}$ alkenecarboxylic halide containing one or more double bond(s) to obtain a compound of the formula Ib, wherein $R_3$ is a $C_{1-20}$ alkanoyloxy group or a $C_{3-22}$ alkenoyloxy group; or if desired, an obtained compound of the formula Ib, wherein $R_3$ represents a hydroxy group, R, R', $R_4$ and $R_5$ are as defined above in a), and X is an oxygen atom or a sulfur atom, is reacted with a $C_{1-5}$ alkyl halide to obtain a compound of the formula Ib, wherein $R_3$ represents a $C_{1-5}$ alkoxy group; or if desired, an obtained compound of the formula Ib, wherein $R_3$ represents a halo atom, R, R', $R_4$ and $R_5$ are as defined above in a), and X is an oxygen atom or a sulfur atom, is reacted with an alkali salt of a $C_{1-5}$ alkanol or a $C_{1-5}$ thioalkanol to obtain a compound of the formula Ib, wherein $R_3$ is a $C_{1-5}$ alkoxy group or a $C_{1-5}$ alkylthio group; or if desired, an obtained compound of the formula Ib, wherein $R_3$ represents a hydroxy group, R, R', $R_4$ and $R_5$ are as defined above in a), and X is an oxygen atom or a sulfur atom, is reacted with a methylsulfonyl halide, a benzenesulfonyl halide or a toluenesulfonyl halide to obtain a compound of the formula Ib, wherein $R_3$ represents a methyl-sulfonyloxy group, a benzene-sulfonyloxy group or a toluene-sulfonyloxy group; and optionally, a compound of the formula Ib obtained by the above methods a) through e) is reacted with an inorganic or organic acid to obtain a pharmaceutically suitable acid addition salt, or one or more nitrogen atom(s) of a compound of the formula Ib is quaternarized with an alkylating agent, or a compound of the formula Ib is reacted with an oxidizing agent to convert one or more nitrogen atom(s) thereof to the corresponding N-oxide.

3. A pharmaceutical composition comprising an oxadiazoline derivative, or an N-oxide, geometrical isomer, optical isomer, or a pharmaceutically suitable acid addition salt or a quaternary ammonium derivative thereof of claim 1, as the active ingredient and one or more pharmaceutically acceptable carriers.

4. A compound selected from the group consisting of:
3-styryl-4-(3-piperidino-2-hydroxpropyl)-$\Delta^2$-1,2,4-oxadiazolin-5-one and pharmaceutically suitable acid addition salts thereof;
3-styryl-4-(3-pyrrolidino-2-hydroxproxypropyl)-$\Delta^2$-1,2,4-oxadiazolin-5-one and pharmaceutically suitable acid addition salts thereof;
3-styryl-4-(3-hexamethyleneimino-2-hydroxypropyl)-$\Delta^2$-1,2,4-oxadiazolin-5-one and pharmaceutically suitable acid addition salts thereof;
3-styryl-4-(3-morpholino-2-hydroxypropyl)-$\Delta^2$-1,2,4-oxadiazolin-5-one and pharmaceutically suitable acid addition salts thereof;
3-styryl-4-[3-(tert.-butylamino)-2-hydroxypropyl]-$\Delta^2$-1,2,4-oxadiazolin-5-one and pharmaceutically suitable acid addition salts thereof;
3-styryl-4-{3-(1,2,3,4-tetrahydro-2-isoquinoyl)-2-hydroxypropyl-$\Delta^2$-1,2,4-oxadiazolin-5-one and pharmaceutically suitable acid addition salts thereof;
3-styryl-4-[3-(2,6-dimethylanilino)-2-hydroxypropyl]-$\Delta^2$-1,2,4-oxadiazolin-5-one and pharmaceutically suitable acid addition salts thereof;
3-(3,4-dimethoxystyrl-4-(3-piperidino-2-hydroxypropyl)-$\Delta^2$-1,2,4-oxadiazolin-5-one and pharmaceutically suitable acid addition salts thereof.

* * * * *